ive forms of $PGE_3$, $PGF_{3\alpha}$, $PGF_{3\beta}$, $PGA_3$, and
United States Patent [19]

Axen

[11] 3,954,851

[45] May 4, 1976

[54] $PGB_3$ ANALOGS

[75] Inventor: Udo F. Axen, Comstock Township, Kalamazoo County, Mich.

[73] Assignee: The Upjohn Company, Kalamazoo, Mich.

[22] Filed: Oct. 30, 1974

[21] Appl. No.: 519,060

Related U.S. Application Data

[63] Continuation of Ser. No. 412,969, Nov. 5, 1973, abandoned, which is a continuation-in-part of Ser. No. 112,032, Feb. 2, 1971, Pat. No. 3,775,462, which is a continuation-in-part of Ser. No. 30,312, April 20, 1970, abandoned.

[52] U.S. Cl. .................. 260/514 D; 260/211 R; 260/247.2 R; 260/268 R; 260/243.05; 260/326.2; 260/408; 260/410; 260/410.5; 260/410.9 R; 260/413; 260/424.9; 260/439 R; 260/448 R; 260/468 D; 260/501.1; 260/501.15; 260/501.17; 260/501.2

[51] Int. Cl.² ................... C07C 61/38; C07C 69/71

[58] Field of Search ........ 260/468, 514, 410, 410.5, 260/410.9, 408, 413

[56] References Cited

FOREIGN PATENTS OR APPLICATIONS

2,118,686  11/1971  Germany ........................... 260/468

OTHER PUBLICATIONS

Green et al., J. Lipid Research, 5, 117, (1964).

*Primary Examiner*—Robert Gerstl

[57] ABSTRACT

This disclosure relates to prostaglandins of the $PG_3$ series including $PGE_3$, $PGF_{3\alpha}$, $PGF_{3\beta}$, $PGA_3$, and $PGB_3$, to various analogs of those in racemic form, and to novel processes for making those. This disclosure also relates to certain fluorine and alkyl substituted analogs and certain acetylenic analogs of $PGE_3$, $PGF_{3\alpha}$, $PGF_{3\beta}$, $PGA_3$, and $PGB_3$ in both racemic and optically active form, and to processes for making those. These various analogs are useful for the same pharmacological purposes as the known optically active forms of $PGE_3$, $PGF_{3\alpha}$, $PGF_{3\beta}$, $PGA_3$, and $PGB_3$, including anti-ulcer, inhibition of platelet aggregation, increase of nasal patency, labor inducement, fertility control, and wound healing.

13 Claims, No Drawings

PGB₃ ANALOGS

CROSS REFERENCE TO RELATED APPLICATION

This application is a continuation of copending application Ser. No. 412,969, filed Nov. 5, 1973, and now abandoned, which is a continuation-in-part of copending application, application Ser. No. 112,032, filed Feb. 2, 1971, and now U.S. Pat. No. 3,775,462, which is a continuation-in-part of copending application Ser. No. 30,312, filed Apr. 20, 1970, and now abandoned.

BRIEF DESCRIPTION OF THE INVENTION

This invention relates to compositions of matter, and to methods and intermediates for producing them. In particular, the several aspects of this invention relate to racemic prostaglandin E₃ (PGE₃), racemic prostaglandin F₃ (PGF₃α and PGF₃β), racemic prostaglandin A₃ (PGA₃), prostaglandin B₃ (PGB₃), to the corresponding acetylenic prostaglandins, 5,6,17,18-dehydro-PGE₃, 5,6,17,18-dehydro-PGF₃α, 5,6,17,18-dehydro-PGF₃β, 5,6,17,18-dehydro-PGA₃, and 5,6,17,18-dehydro-PGB₃; to analogs of those prostaglandins and 5,6,17,18-dehydro-prostaglandins; to processes for producing racemic PGE₃, PGF₃α, PGF₃β, PGA₃, PGB₃, the corresponding 5,6,17,18-dehydro-prostaglandins, and the analogs thereof; ot processes for resolving the racemates into the d- and l-forms; and to chemical intermediates useful in those methods.

Optically active PGE₃ (the natural or d-configuration) is a known substance. Bergstrom, Science 157, 382 (1967); Samuelson, J. Amer. Chem. Soc., 85, 1878 (1963). Optically active PGF₃ (α and β), obtained by the borohydride reduction of optically active PGE₃ is also a known substance; Samuelson, Biochemica Biophysica Acta, 84, 707 (1964); so also is optically active PGA₃. British Specification 1,097,533. Optically active PGE₃, optically active PGF₃α, and optically active PGF₃β are also disclosed in British specification 1,040,544.

The prior art methods for producing prostaglandins are costly and difficult, the necessary biological materials are limited, and the methods are not adaptable to production of a wide variety of prostaglandin intermediates and analogs.

It is the purpose of this invention to provide processes for the production of compounds with prostaglandin-like activity in substantial amounts and at reasonable cost. The useful compounds produced according to the processes of this invention comprise racemic PGE₃, racemic PGF₃α, racemic PGF₃β, racemic PGA₃, racemic PGB₃, the corresponding 5,6,17,18-dehydro-prostaglandins, and other hitherto unavailable racemic and optically active analogs thereof such as the enantiomorphs (d- and l-forms) of PGB₃ and the 5,6,17,18-dehydro compounds.

PGE₃ has the following structure:

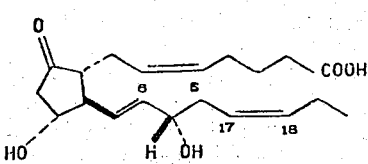

I

PGF₃α has the following structure:

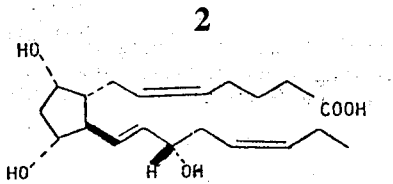

II

PGF₃β has the following structure:

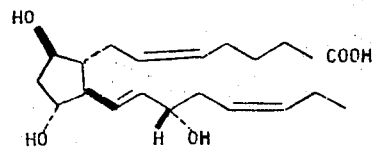

III

PGA₃ has the following structure:

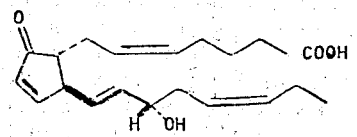

IV

PGB₃ has the following structure:

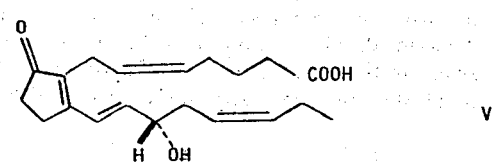

V

The above formulas represent the natural configuration. Racemic PGE₃, PGF₃α, PGF₃β, PGA₃, and PGB₃ are each represented by the combination of one of the above formulas and the mirror image (enantiomorph) of that formula. See Nature, 212, 38 (1966) for discussion of the stereochemistry of the prostaglandins.

In formulas I, II, III, IV, and V, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

PGE₃, PGF₃α, PGF₃β, PGA₃, and PGB₃ are derivatives of prostanoic acid which has the following structure and atom numbering:

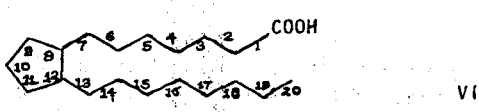

VI

A systematic name for prostanoic acid is i-[(2β-octyl)-cyclopent-1α-yl]heptanoic acid.

Compounds similar to formula VI but with carboxyl-terminated side chains attached to the cyclopentane ring in beta configuration are designated 8-iso-prostanoic acids, and have the following formula:

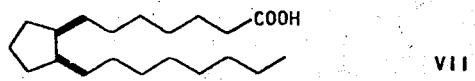

VII

A systematic name for iso-prostanoic acid is 7-[(2β-octyl)cyclopent-1β-yl]heptanoic acid.

Prostaglandin E₃ and its analogs and isomers produced according to the process of this invention are represented by the formula:

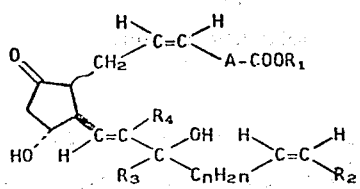

VIIIe wherein R₁ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the β-position with 3 chloro, 2 or 3 bromo, or 1, 2, or 3 iodo; wherein R₂ is alkyl of one to 4 carbon atoms, inclusive, substituted with zero to 3 fluoro; wherein R₃ and R₄ are hydrogen or alkyl or one to 4 carbon atoms, inclusive; wherein n is an integer of one to 4, inclusive; wherein A is alkylene of one to 10 carbon atoms, inclusive, substituted with zero to 2 fluoro, and with one to 5 carbon atoms, inclusive, between —COOR₁ and

and pharmacologically acceptable salts thereof wherein R₁ is hydrogen.

Prostaglandin F₃ and its analogs and isomers produced according to the processes of this invention are represented by the formula:

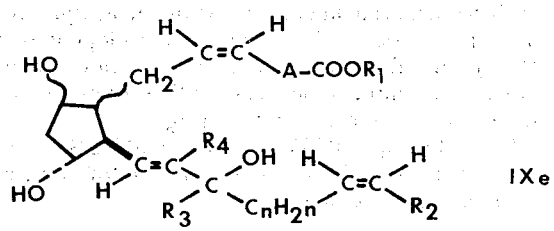

IXe wherein R₁, R₂, R₃, R₄, and A are as defined above for formula XIIIe, and pharmacologically acceptable salts thereof when R₁ is hydrogen.

Prostaglandin A₃ and its analogs and isomers produced according to the process of this invention are represented by the formula:

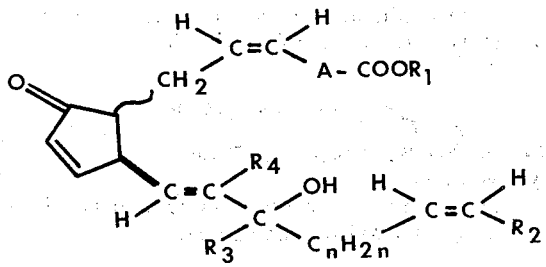

Xe wherein R₁, R₂, R₃, R₄, and A are as defined above for formula VIIIe, and the pharmacologically acceptable salts thereof wherein R₁ is hydrogen.

Prostaglandin B₃ and its analogs and isomers (including its enantiomorphs) produced according to the processes of this invention are represented by the formula:

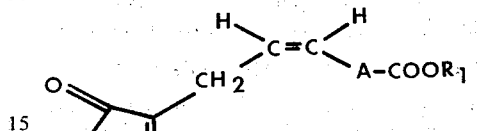
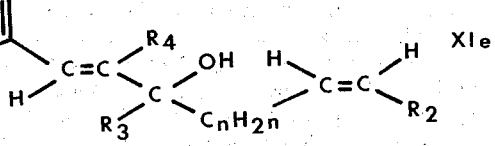

XIe wherein R₁, R₂, R₃, R₄, and A are defined above for formula VIIIe, and pharmacologically acceptable salts thereof wherein R₁ is hydrogen.

The wavy line, ~, as used above, and elsewhere herein, includes both configurations, i.e., alpha and beta, or endo or exo. The word "racemic" indicates an equal mixture of a compound of the formula shown, which is the natural configuration, and its enantiomorph.

Compounds of formula VIIIe, IXe, Xe, and XIe have their counterpart where the cis-ethylenes are dehydro i.e., ethynylene, These dehydro analogs here designated as VIIId, IXd, Xd, and XId, are intermediates, as will be shown, for making the compounds of formulas VIIIe, IXe, Xe, and XIe. Racemic dehydro compounds give racemic final products. An enantiomorph of the dehydro compound (the configuration as shown or the mirror image thereof) gives the corresponding enantiomorph of the final compound.

Also included in formulas VIII, IX, X and XI are separate isomers wherein the side chain hydroxy is in R or S configuration. All of the compounds encompassed by formulas VIII, IXX, and X have the trans —CH=C-R₄—CR₃OH— side chain attached in beta configuration.

Formulas VIIIe, IXe, Xe, and XIe present PGE₃, PGF₃, PGA₃, and PGB₃, respectively, when in these formulas R₁, R₃, and R₄ are each hydrogen, n is 1, R₂ is ethyl, A is trimethylene, the attachment of —CH₂—CH=CH—A—COOR₁ to the cyclopentane ring is in alpha configuration, and the configuration of the side chain hydroxy is S.

With regard to formulas VIII to XI, inclusive, examples of alkyl of one to 4 carbon atoms, inclusive, are methyl, ethyl, propyl, butyl, and isomeric forms thereof. Examples of alkyl of one to 8 carbon atoms, inclusive, are those given above, and pentyl, hexyl, heptyl, octyl, and isomeric forms thereof. Examples of alkyl of one to 10 carbon atoms, inclusive, are those given above, and nonyl, decyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2- dimethylcyclopwntyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl, Examples of aralkyl of 7 to 12 carbon atoms, inclusive, are benzyl, phenethyl, 1-phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butyl-phenyl, 2,5-dimethylphenyl, 4-chloro-2-methylphenyl, and 2,4-dichloro-3-methylphenyl.

Examples of alkylene of one to 10 carbon atoms, inclusive, are methylene, ethylene, trimethylene, tetramethylene, pentamethylene, and isomeric branched chain forms thereof, 1-, 2-, and 3-methylpentamethylene, 1-, 2-, 3-ethylpentamethylene, 1-, 2-, and 3-propylpentamethylene, 1-, 2-, and 3-butylpentamethylene, and 1-, 2-, and 3-pentylpentamethylene.

Examples of alkyl of one to 4 carbon atoms, inclusive, substituted with one to 3 fluoro, are 2-fluoroethyl, 2-fluorobutyl, 3-fluorobutyl, 4-fluorobutyl, 3,4-difluorobutyl, 2,2,2-trifluoroethyl, and 4,4,4-trifluorobutyl.

Examples of alkylene of one to 10 carbon atoms, inclusive, substituted with one or 2 fluoro, have the formulas $-CH_2CHF-$, $-CH_2CF_2-$, $-CH_2CH_2CHFCH_3-$, $-CH_2CH_2CH_2CF_2-$, $-CH_2CHCH_2CHF-$, $-CH_2CH_2CH_2CHFCHF-$, $-CH_2CH_2CH_2CH_2CF_2-$, $-CH_2CH_2CH_2CF_2CH_2-$, and $CH_2CH_2CF_2CH_2CH_2-$.

$PGE_2$, $PGF_{2\alpha}$, $PGF_2\beta$, $PGA_2$, and $PGB_2$, and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of $PGE_2$, $PGF_2\beta$, and $PGA_2$ as measured, for example, in anesthetized (pentobarbital sodium) pentolinium-treated rats with indwelling aortic and right heart cannulas; pressor activity, similarly measured, for $PGF_2\alpha$; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of $PGE_2$ and $PGA_2$ as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of $PGE_2$ and $PBG_2$, stimulation of epidermal proliferation and keratinization as shown when applied in culture to embryonic chick and rat skin segments.

Optically active $PGE_3$, and its esters and pharmacologically acceptable salts, are also extremely potent in causing the same biological responses as $PGE_2$. Horton et al., Brit. J. of Pharm. and Chemotherapy, 21, 182 (1963); Bergstrom et al., acta physiol. science, 59, 493 (1963); Heinberg et al., J. Clinic. investigation, 43, 1533 (1964); Bergstrom et al., acta physiol. science, 60, 170 (1964); and Sandberg et al., Acta Obstetrica et Gynecolojica Science, 43, 95 (1964). Optically active $PGF_3$ and $PGA_3$ which are obtained from optically active $PGE_3$ also cause the same biological responses as $PGF_2$ and $PGA_2$.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially $PGE_2$, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application. $PGE_3$ is similarly useful when administered in equivalent doses.

$PGE_2$ and $PGA_2$ are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection of infusion in the range about 0.1 to about 20 mg. per kg. of body weight per day, the exact dose depending on the age, weight, and condition of the patient or animal, and on the frequency and route of administration. $PGE_3$ and $PGA_3$ are similarly useful when administered in equivalent doses.

$PGE_2$, $PGA_2$, $PGF_{2\alpha}$, and $PGF_2\beta$ are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.004 to about 20 mg. per kg. of body weight per day are used, the exact dose depending on the age, weight, and condition of the patient or animal, and on the frequency and route of administration. $PGE_3$, $PGA_3$, $PGF_{3\alpha}$, and $PGF_3\beta$ are similarly useful when administered in equivalent doses.

$PGE_2$, $PGA_2$, $PGF_{2\alpha}$, and $PGF_2\beta$ are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the ciruclating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplatns. $PGE_3$, $PGA_3$, $PFG_{3\alpha}$, and $PGF_{3\beta}$ are similarly useful when administered in equivalent doses.

$PGE_2$ is extremely potent in causing stimulation of smooth muscle, and is also highly active in potentiating other known smooth muscle stimulators, for example, oxytocic agents, e.g., oxytocin, and the various ergot alkaloids including derivatives and analogs thereof. Therefore $PGE_2$ is useful in place of or in combination with less than usual amounts of these known smooth muscle stimulators, for example, to relieve the symptoms of paralytic ileus, to control or prevent atonic uterine bleeding after abortion or delivery, to aid in expulsion of the placenta, and during the puerperium. For these purposes, $PGE_2$ is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal. $PGE_3$ is similarly useful when administered in equivalent doses.

$PGE_2$, $PGA_2$, and $PGF_{2\beta}$ are useful as hypotensive agents to reduce blood pressure in mammals, including man. For this purpose, the compounds are administered by intravenous infusion at the rate about 0.01 to about 50 µg. per kg. of body weight per minute or in single or multiple doses of about 25 to 500 µg. per kg. of body weight total per day. $PGE_3$, $PGA_3$, and $PGF_{3\beta}$ are similarly useful when administered in equivalent doses.

$PGE_2$, $PGF_{2\alpha}$, and $PGF_{2\beta}$ are useful in place of oxytocin to induce labor in pregnant animals, including man, cows, sheep, and pigs, at or near term, or in pregnant animals with intrauterine death of the fetus from about 20 weeks to term. For this purpose, the compound is infused intravenously at a dose 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. $PGE_3$, $PGF_{3\alpha}$, and $PGF_{3\beta}$ are similarly useful when administered in equivalent doses.

$PGF_{2\alpha}$, $PGF_{2\beta}$, and $PGE_2$ are useful for controlling the reproductive cycle in ovulating female mammals, including humans and animals such as monkeys, rats, rabbits, dogs, cattle, and the like. For that purpose, $PGF_{2\alpha}$ is administered systemically at a dose level in the range 0.01 mg. to about 20 mg. per kg. of body weight of the female mammal, advantageously during a span of time starting approximately at the time of ovulation and ending approximately at the time of menses or just prior to menses. $PGE_3$, $PGF_{3\alpha}$, and $PGF_{3\beta}$ are similarly useful when administered in equivalent doses.

As mentioned above, $PGE_2$ is a potent antagonist of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism. $PGE_3$ is similarly useful when administered in equivalent doses.

$PGE_2$ and $PGB_2$ promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts. $PGE_3$ and $PGB_3$ are similarly useful when administered in equivalent doses.

For these purposes, these compounds as well as the compounds of the invention are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of these being used in the combination at the usual concentration suitable for its use alone.

Racemic $PGE_3$, racemic $PGF_3$, racemic $PGF_{3\beta}$, and racemic $PGA_3$, each are useful for the purposes described above for the optically active compounds, but these racemic compounds offer the enormous advantage of being available in unlimited quantities at much lower cost. Racemic $PGB_3$ has like advantages and is useful for the same purposes as $PGB_3$. Moreover, these racemic compounds are easier to purify since they are produced by chemical reactions rather than by extraction from biological materials or enzymatic reaction mixtures.

The PGE$_3$, PGF$_3$, PGA$_3$, and PGB$_3$ analogs and isomers cause corresponding biological responses and are useful for corresponding purposes as PGE$_3$, PGF$_3$, PGA$_3$, and PGB$_3$, respectively.

To obtain the optimum combinations of biological response specificity and potency, certain compounds within the scope of formulas VIIIe and IXe are preferred. As discussed above, those formulas represent the PGE$_3$-type compounds and the PGF$_3$ -type compounds, respectively. Referring to formulas VIIIe and IXe, when —CH$_2$—CH=CH—A—COOR$_1$ is attached in alpha configuration and, in the case of formula IXe, when the ring hydroxy is also attached in alpha configuration, the sterochemistry is typical of the known optically active PGE$_3$ and PGF$_{3\alpha}$. According to this invention, preferred formula VIIIe and IXe compounds are those wherein —CH$_2$—CH=CH—A—COOR$_1$ and ring hydroxy are alpha, $n$ is 1 and A is trimethylene, R$_4$ is hydrogen and R$_3$ is hydrogen or methyl and R$_2$ is ethyl. These preferred compounds exhibit superior biological response specificity and/or potency.

Certain compounds within the scope of formulas VIIIe to XIe are especially useful for one or more of the purposes stated above, because they have a substantially longer duration of activity than other compounds within the generic formulas, including PGE$_3$, PGF$_{3\alpha}$, PGF$_{3\beta}$, PGA$_3$, and PGB$_3$, and because they can be administered orally, sublingually, intravaginally, buccally, or rectally, rather than by the usual intravenous, intramuscular, or subcutaneous injection or infusion as indicated above for the uses of these known prostaglandins and the other compounds encompassed by formulas VIIIe to XIe. These qualities are advantageous because they facilitate maintaining uniform levels of these compounds in the body with fewer, shorter, or smaller doses, and make possible self-administration by the patient.

With reference to formulas VIIIe to XIe, these special compounds include those wherein A is —(CH$_2$)$_b$—Z—, wherein $b$ is zero, one, 2, or 3, and Z is ethylene substituted by one or 2 fluoro, methyl, or ethyl, or by one alkyl of 3 or 4 carbon atoms. These special compounds also include those wherein R$_2$ is ethyl, propyl, isopropyl, isobutyl, tert-butyl, 3,3-difluorobutyl, 4,4-difluorobutyl, or 4,4,4-trifluorobutyl. These special compounds also include those wherein A is —(CH$_2$)$_b$—Z— as above defined, and R$_2$ is ethyl, propyl, isopropyl, isobutyl, tert-butyl, 3,3-difluorobutyl, 4,4-difluorobutyl, or 4,4,4-trifluorobutyl. Especially preferred among these special compounds are those wherein R$_3$ and R$_4$ are both hydrogen.

In the case of Z, the divalent ethylene group, —CH$_2$—CH$_2$—, is substituted on either or both carbon atoms, i.e., alpha and/or beta to the carboxylate function. For example, Z is —CH$_2$—CHF—, —CHF—CH$_2$—, —CH$_2$—CF$_2$—, —CHF—CHF—, —CH$_2$—CH(CH$_3$)—, —CH(CH$_3$)—CH$_2$—, —CH$_2$—C(CH$_3$)$_2$—, —C(CH$_3$)$_2$—CH$_2$—, —CH(CH$_3$)—CH(CH$_3$)—, and similarly for ethyl, and for one fluoro and one methyl, one fluoro and one ethyl, and one methyl and one ethyl. Z is alternatively ethylene substituted on either carbon atom with propyl, isopropyl, butyl, isobutyl, sec-butyl, or tert-butyl.

Although all of the special compounds just described have the special advantages of long duration and oral, sublingual intravaginal, and rectal routes of administration, there is a still more limited group of compounds encompassed by these formulas which have these qualities in a particularly high degree. Those are the compounds wherein A is —CH$_2$—Z—, i.e., wherein $b$ in —(CH$_2$)$_b$—Z— is one, especially when Z is ethylene with one fluoro or methyl, with 2 fluoro or 2 methyl on the same carbon atoms, or with butyl, isobutyl, sec-butyl, or tert-butyl on the carbon atoms alpha (adjacent) to the carboxylate function, the compounds wherein R$_2$ is —C(CH$_3$)$_3$, —CH$_2$CH(CH$_3$)$_2$, —CH$_2$CF$_3$, —CH$_2$CHF$_2$, or —CH$_2$CF$_2$CH$_3$, and the compounds wherein both A and R are both defined in these more limited ways.

Racemic PGE$_3$, racemic PGF$_{3\alpha}$, racemic PGF$_{3\beta}$, racemic PGA$_3$, racemic PGB$_3$, and the other compounds encompassed by formulas VIIIe and XIe, are used for the pusposes described above in the free acid form, in ester form, or in pharmacologically acceptable salt form. When the ester form is used, the ester is any of those within the above definition of R$_1$. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these formula VIIIe, IXe, Xe, and XIe compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and aralifphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidone, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amine-2-ethyl-1,3-propanediol. 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epimephrine, procaine, and the like.

Examples of suitable pharmcologically acceptable quaternary ammoniium cations are tetramethylammonium, tetramethylammonium, tetraethylammonium, benzyltrimethylammonium, phenyltriethylammonium, and the like.

As discussed above, the compounds of formulas VIIIe to XIe are administered in various ways for various purposes; e.g., intravenously, intramuscularly, subcutaneously, orally, intravaginally, rectally, buccally, subligually, topically, and in the form of sterile implants for prolonged action.

For intravenous injection or infusion, sterile aqueous isotonic solutions are preferred. For the purpose, it is preferred because of increased water solubility that $R_1$, in the formula VIIIe to XIe compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

Racemic $PGE_3$, racemic $PGF_{3\alpha}$, racemic $PGF_{3\beta}$, racemic $PGA_3$, racemic $PGB_3$, and the other compounds encompassed by formulas VIIIE, IXe, Xe, and XIe are produced by the reactions and procedures described hereinafter. As intermediates there are produced the corresponding 5,6,17,18-dehydroprostaglandins VIIId, IXd, Xd, and XId which in the free acid or salt forms are useful also for the purposes given above. The enantiomorphs of the VIII, IX, X, and XI compounds are formed either by resolution of the final product racemate or a racemic intermediate.

Racemic $PGF_{3\alpha}$, racemic $PGF_{3\beta}$, and the other $PGF_3$-type compounds encompassed by formula IX are prepared by carbonyl reduction of the corresponding $PGE_3$-type compounds encompassed by formula VIII. For example, carbonyl reduction of racemic $PGE_3$, VIIIe, gives a mixture of racemic $PGF_{3\alpha}$, IXe$\alpha$, and racemic $PGF_{3\beta}$, IXe$\beta$. The corresponding 5,6,17,18-dehydro $PGF_3$-type compounds, IXd, are produced in a like manner from 5,6,17,18-dehydro-$PGE_3$-type compounds, VIIId, and by hydrogenation of the acetylenic bonds are converted to the corresponding $PGF_3$-type compounds, IXe.

These ring carbonyl reductions are carried out by methods known in the art for ring carbonyl reductions of known prostanoic acid derivatives. See, for example, Bergstrom et al., Arkiv Kemi, 19, 563 (1963), and Acta Chem. Scand. 16, 969 (1962), and British Specification No. 1,097,533. Any reducing agent is used which does not react with carbon-carbon double bonds or ester groups. Preferred reagents are lithium (tri-tert-butoxy) aluminum hydride and the metal borohydrides, especially sodium, potassium and zinc borohydrides. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research, 5, 117 (1964). Especially preferred as separation methods are partition chromatographic procedures, both normal and reversed phase, preparative thin layer chromatography, and countercurrent distribution procedures. They can be applied either before or after the hydrogenation of the acetylenic bonds.

Racemic $PGA_3$ and the other $PGA_3$-type compounds encompassed by formula X are prepared by acidic dehydration of the corresponding $PGE_3$-type compounds encompassed by formula VIII. For example, acidic dehydration of racemic $PGE_3$, VIIIe, gives racemic $PGA_3$, Xe. The corresponding 5,6,17,18-dehydro-$PGA_3$-type compounds Xd, are produced in a like manner from 5,6,17,18-dehydro-$PGE_3$-type compounds, VIIId, and by hydrogenation of the acetylenic bonds are converted to $PGA_3$-type compounds, Xe.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, p. 161 (1967); and British Specification 1,097,533. Alkanoic acids of 2 to 6 carbon atoms, inclusive, especially acetic acid, are preferred acids for this acidic dehydration. They can be applied either before or after the hydrogenation of the acetylenic bonds.

Racemic $PGB_3$ and the other compounds encompassed by formula XIe are prepared by basic dehydration of the corresponding $PGE_3$-type compounds encompassed by formula VIIIe or by contacting the corresponding $PGA_3$-type compounds encompassed by formula Xe with base. For example, both racemic $PGE_3$, VIIIe, and racemic $PGA_3$, Xe, give racemic $PGB_3$, XIe, on treatment with base. Presumably the base first causes dehydration of the $PGE_3$ to $PGA_3$, and then causes the ring double bond of $PGA_3$ to migrate to a new position. The corresponding 5,6,17,18-dehydro-$PGB_3$-type compounds, XId, are produced in a like manner from 5,6,17,18-dehydro-$PGE_3$-, VIIId, or 5,6,17,18-dehydro-$PGA_3$-type compounds, Xd, and by hydrogenation of the acetylenic bonds are converted to $PGB_3$-compounds, XId.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The $PGE_3$-type or $PGA_3$-type compound is maintained in such a reaction medium until no further $PGB_3$-type compound is formed, as shown by the characteristic ultraviolet light absorption for the $PGB_3$-type compound. They can be applied either before or after the hydrogenation of the acetylenic bonds.

These various transformations of the $PGE_3$-type compounds of formulas VIIIe to the $PGF_3$-type, IXe, $PGA_3$-type, Xe, and $PGB_3$-type, XIe, compounds are shown in Chart A, wherein $R_1$, $R_2$, $R_3$, $R_4$, A, and are as defined above. The same transformation can be applied to the 5,6,17,18-dehydro-$PGE_3$-type compounds, VIIId, as shown in Chart A-1. If desired, the 5,6,17,18-dehydro-$PGA_3$-type compounds, Xd, can be converted to $PGA_3$-type compounds, Xe, by hydrogenation by the procedures of step 8 and 8a, infra.

Racemic $PGE_3$ and the other $PGE_3$-type compounds encompassed by formula VIII are prepared by the multi-step processes outlined in Charts B, C, and D.

CHART A
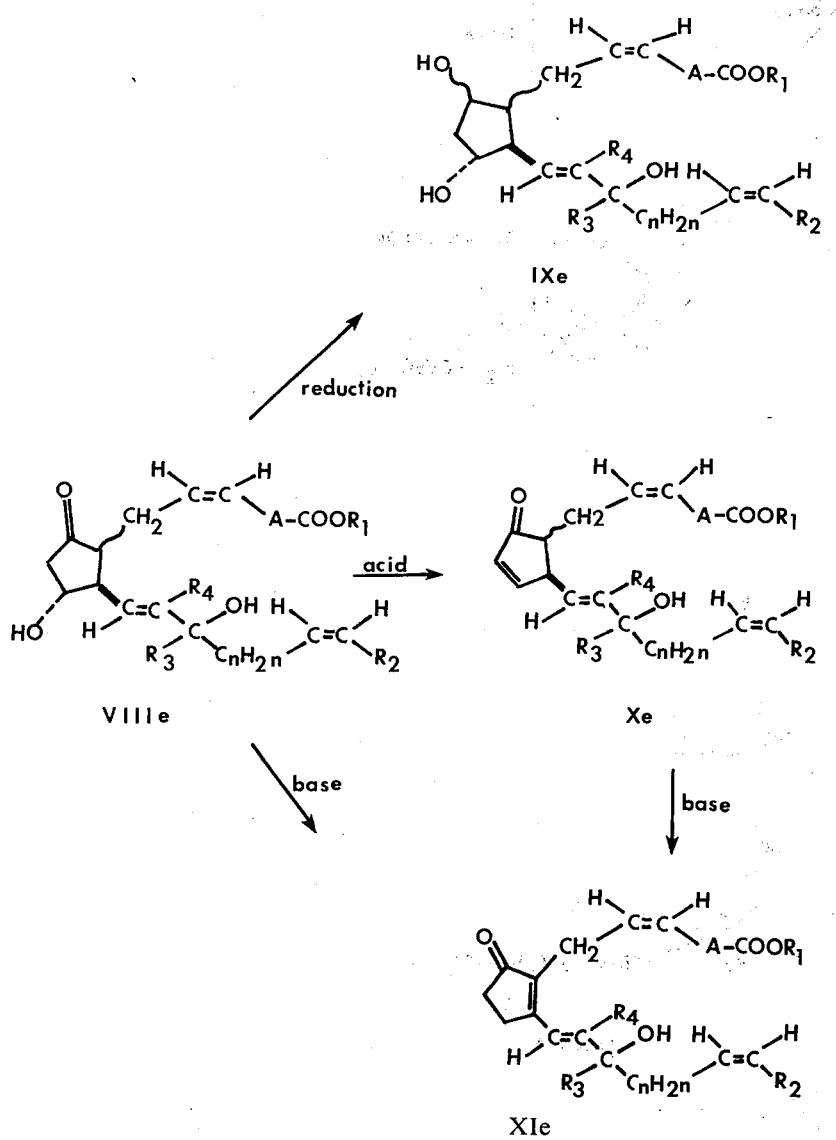
CHART A-1
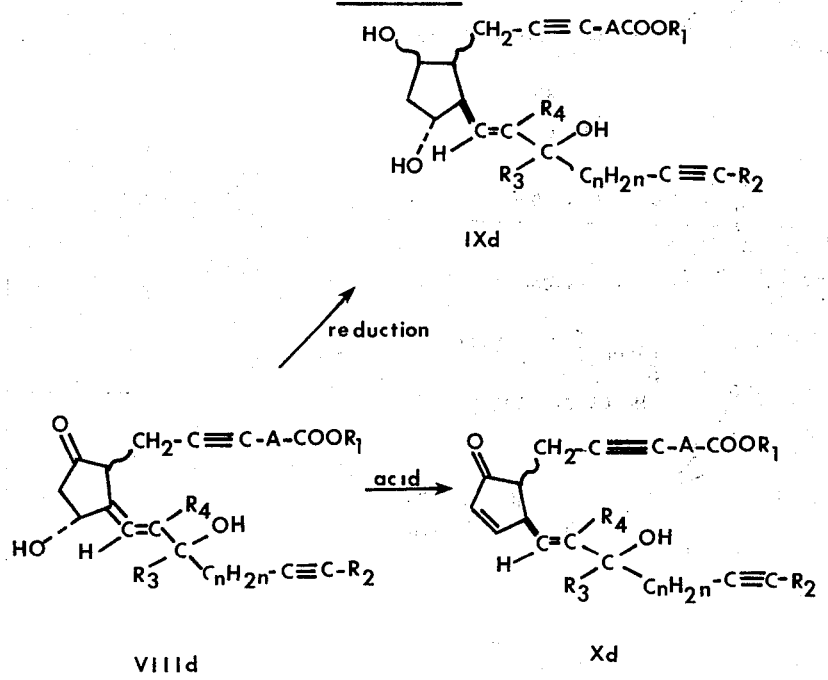

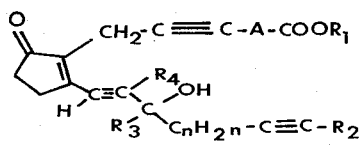
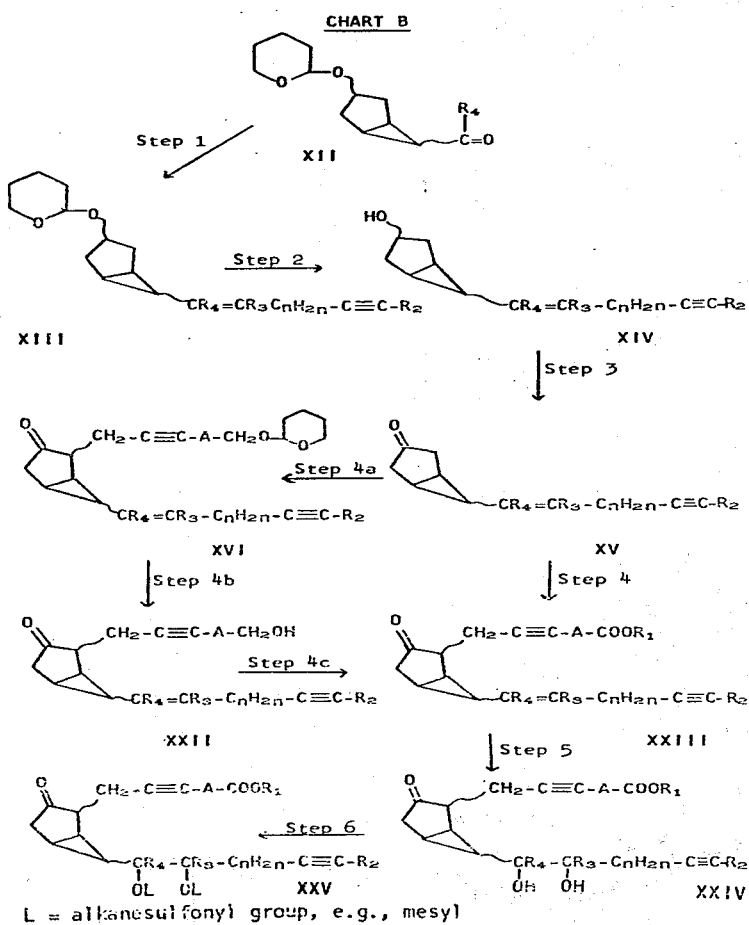

CHART C

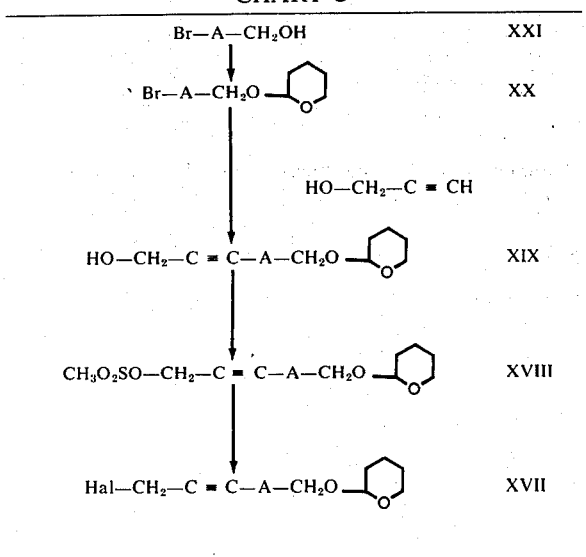

The bicyclic compound of formula XII in Chart B is the initial reactant in these multi-step processes. It exists in two isomeric forms, exo and endo with respect to the attachment of the —$CR_4O$ moiety. It also exists in two isomeric forms with respect to the attachment of the tetrahydropyranyloxy group making in all four isomeric forms. Each of those isomers separately or mixtures thereof are used as reactants according to this invention to produce substantially the same final $PGE_3$-type or 5,6,17,18-dehydro$PGE_3$-type product mixture.

In Belgian Patent No. 702,477; reprinted in Farmdoc Complete Specifications, Book 714, No. 30,905, page 313, March 12, 1968, the reaction sequence leading to exo form of compound XII is as follows: The hydroxy of 3-cyclopentenol is protected, for example, with a tetrahydropyranyl group. Then a diazoacetic acid ester is added to the double bond to give an exo-endo mixture of a bicyclo[3.1.0]hexane substituted at 3 with the protected hydroxy and at 6 with an esterified carboxyl. The exo-endo mixture is treated with a base to isomerize the endo isomer in the mixture to more of the exo

CHART D

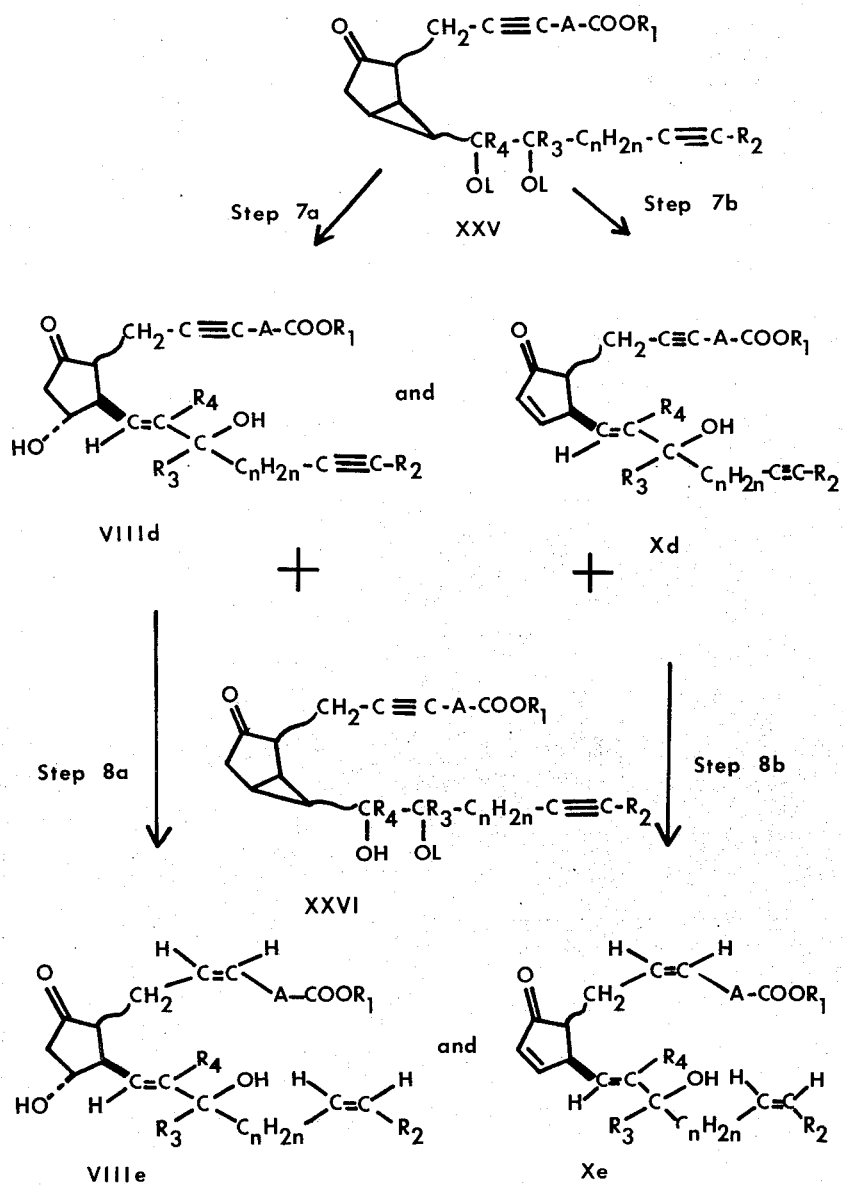

isomer. Next, the carboxylate ester group at 6 is transformed to an aldehyde group or ketone group,

wherein $R_4$ is as defined above.

In the first step of the process (Chart B), the aldehyde group or keto group is transformed by the Wittig reaction to a moiety of the formula $-CR_4=CR_3C_nH_{2n}-C\equiv C-R_2$ which is in exo configuration relative to the bicyclo ring structure, and is the same as shown in formula XIII. In step 2, the protective group is removed to regenerate the 3-hydroxy (XIV) which is then oxidized in step 3, for example, by the Jones reagent, to give the exo compound XV.

Separation of the cis-exo and trans-exo isomers of XV can be effected by the procedures described in said Belgian patent. However, as mentioned above, that separation is usually not necessary since the cis-trans mixture is useful as a reactant in the next process step.

The process described in said Belgian patent No. 702,477 for producing the exo form of bicyclic compound XII uses as an intermediate, the exo form of a bicyclo[3.1.0]hexane substituted at 3 with a protected hydroxy, e.g., tetrahydropyranyloxy and at 6 with an esterified carboxyl. When the corresponding endo compound is substituted for that exo intermediate, the Belgian patent process leads to the endo form of bicyclic compound XII. That endo intermediate used in the Belgian patent process has the formula:

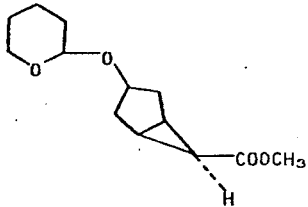

XXVII

Compound XXVII is prepared by reacting endo-bicyclo[3.1.0]hex-2-ene-6-carboxylic acid methyl ester with diborane in a mixture of tetrahydrofuran and diethyl ether, a reaction generally known in the art, to give endobicyclo[3.1.0]hexan-3-ol-6-carboxylic acid methyl ester which is then reacted with dihydropyran in the presence of a catalytic amount of $POCL_3$ to give the desired compound. This is then used as described in said Belgian patent to produce the endo form of bicyclic compound XII.

Using this endo form of bicyclic compound XII as the starting material, steps 2 and 3 produce mixtures of endo-cis and endo-trans. These can be separated as described for the separation of exo-cis and exo-trans XV, but this separation is usually not necessary since, as mentioned above, the cis-trans mixture is useful as reactant in the next process step.

In the Wittig reaction, (Step 1), the other starting compound is an organic chloride or bromide, or iodide of the formula

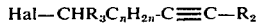  XXVIII

This can be prepared from the corresponding alcohol

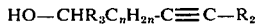  XXIX by processes already known in the art, for example, by reacting compound XXIX with triphenylphosphine and N-bromosuccinimide.

Acetylenic alcohols of formula XXIX are generally known in the art, for example, 3-pentyn-1-ol, 3-hexyn-1-ol, 4-hexyn-1-ol, 2-methyl-3-pentyn-1-ol, 2,3-dimethyl-4-pentyn-1-ol, 6-octyn-1-ol, 6-nonyn-1-ol, 4-undecyn-1-ol, 6-dodecyn-1-ol, 5-tetradecyn-1-ol, and the like. Others where $R_3$ is methyl, ethyl, propyl, butyl, or the isomers thereof can be made by reacting an acetylenic aldehyde of the formula

  XXX with the appropriate Grignard reagent, $BrMgR_3$. These acetylenic aldehydes can be made by oxidizing the corresponding alcohol, for example, those listed above, with a Jones reagent, Collins reagent, a Moffatt oxidation or the like. The aldehyde is then reacted with $BrMgR_3$ to prepare acetylenic alcohols of formula XXIX. Compounds thus obtainable include 4-hexyn-2-ol, 4-heptyn-2-ol, 5-heptyn-2-ol, 3-methyl-4-hexyn-2-ol, 3,4-dimethyl-5-hexyn-2-ol, 7-nonyn-2-ol, 7-decyn-2-ol, 5-dodecyn-2-ol, 7-tridecyn-2-ol, 5-heptyn-3-ol, 5-octyn-3-ol, 6-octyn-3-ol, 8-undecyn-3-ol, 6-tridecyn-3-ol, 8-tetradecyn-3-ol, and the like. Still other alkyn-1-ols according to formula XXIX ($R_3$ = hydrogen) can be made by condensing an omega-alkyl-1-ol of the formula

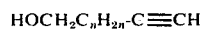  XXXI with an alkyl halide, $HalR_2$, using lithium and ammonia as the condensing agent; still others by condensing a protected halohydrin of the formula

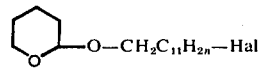  XXXII with a 1-alkyl, $HC\equiv CR_2$. Again lithium and ammonia can be used as the condensing agent.

The protective tetrahydropyranyl group

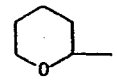

can then be removed by acid hydrolysis to form an acetylenic alcohol of formula XXIX. The latter process is particularly useful where $R_2$ is a halo substituted alkyl. The 1-alkyn, $HC\equiv CR_2$, can be made by condensing acetylene with or sodium acctslide with an alkyl halide, $R_2Hal$ where $R_2$ is as given above.

The transformation of bicyclo-ketone-olefin XXIII to glycol XXIV (Step 5, Chart B) is carried out by reacting olefin XXIII with a hydroxylation reagent. Hydroxylation reagents and procedures for this purpose are known in the art. See, for example, Gunstone, Advances in Organic Chemistry, Vol. 1, pp. 103—147, Interscience Publishers, New York, N. Y. (1960). Various isomeric glycols are obtained depending on whether olefin XXIII is cis or trans and endo or exo, and on whether a cis or a trans hydroxylation reagent is used. Thus endo-cis olefin XXIII gives a mixture of two isomeric erythro glycols of formula XXIV with a cis hydroxylation agent, e.g., potassium permanganate. The endo-cis olefins and the endo-trans olefins XXIII give similar mixtures of two threo isomers with cis and trans hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Charts B, C, and D to produce final products of formulas VIIIe and Xe, and then, according to Chart A, to produce the other final products of this invention. Thus the various isomeric glycol mixtures encompassed by formula XXIV produced from the various isomeric olefins encompassed by formula XXIII are all useful for these same purposes.

In step 4 the other starting material is a haloalkynoic ester of the formula

    XXXIII wherein Hal is chlorine, bromine, or iodine. In effecting this step any of the alkylation procedures known in the art to be useful for alkylating cyclic ketones with alkyl halides, especially haloalkynoic esters, can be used for the transformation of XV to XXIII. See, for example, the above mentioned Belgian patent No. 702,477 for procedures useful here and used there to carry out similar alkylations.

For this alkyation, it is preferred that Hal be bromo, or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1.2-dimethoxyethane. Otherwise, procedures for producing and isolating the desired formula XXIII compound are within the skill of the art.

This alkylation procedure produces a mixture of alpha and beta alkylation products, i.e., a mixture of formula XXIII products wherein part has the —CH$_2$C≡C-A-COOR$_1$ moiety attached in alpha configuration and wherein part has that moiety attached in beta configuration. When about one equivalent of base per equivalent of formula XV ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Charts B and D. Silica gel chromatography is preferred for this separation.

An alternative alkylation procedure is shown in steps 4a, 4b, and 4c. The alkylating agent XVII is reacted with the bicyclo-ketone-olefin XV by the alkylation procedure described above for step 4.

The alkylating agent of formula XVII is prepared by the series of reactions shown in Chart C. The initial reactants, Br—A—CH$_2$OH, are omega bromoalcohols which are known in the art or can be prepared by methods known in the art. For example, when A in the final product is to be trimethylene as it is in racemic PGE$_3$, the necessary 4-bromobutanol is prepared by reacting tetrahydrofuran with hydrogen bromide.

To illustrate the availability of the other bromoglycols of formula XXI (Chart C), consider the above-described special compounds of formula VIIIe, wherein A is —(CH$_2$)$_b$—Z—, wherein $b$ is zero, one, 2, or 3, and Z is ethylene substituted by one or 2-fluoro, methyl, or ethyl, or by one alkyl or 3 or 4 carbon atoms. These omega-bromoalcohols, Br—(CH$_2$)$_b$—Z—CH$_2$OH, are prepared by starting with the appropriate succinic acid, HOOC—Z—COOH, all of which are known or easily accessible by known methods. These succinic acids are transformed to the corresponding anhydrides by known procedures. Each anhydride is then reacted with an alkanol, for example, methanol, to give the corresponding succinic acid half ester, e.g., HOOC—Z—COOCH$_3$. When Z is unsymmetrical, e.g., substituted with one fluoro, a mixture of isomeric half esters is obtained, HOOC—Z—COOCH$_3$ and CH$_3$—OOC—Z—COOH, which is separated to give the desired isomer.

When it is desired that $b$ is Br—(CH$_2$)$_b$—Z—CH$_2$OH be zero, the succinic acid half ester is subjected to the Hunsdiecker reaction, thereby producing Br—Z—COOCH$_3$, which is reduced by lithium aluminum hydride to Br—Z—CH$_2$OH. When $b$ is to be one, the carboxyl group of the succinic acid half ester is changed to acid chloride with thionyl chloride, to aldehyde by the Rosenmund reduction, to alcohol with sodium borohydride, and to —CH$_2$Br with PBr$_3$, giving BR—CH$_2$—Z—COOCH$_3$, which is then reduced to Br—CH$_2$—Z—CH$_2$OH with lithium aluminum hydride. When $b$ is to be 2 or 3, the succinic acid half ester is subjected once or twice to the Arndt-Eistert reaction to produce HOOC—CH$_2$—Z—COOCH$_3$ or HOCC—CH$_2$—Z—COOCH$_3$, which is then subjected to the same series of reactions given above to give Br—CH$_2$CH$_2$—Z—CH$_2$OH or Br—CH$_2$CH$_2$CH$_2$—Z—CH$_2$OH.

Referring again to Chart C, the several process steps, XXI to XX, XX to XIX, XIX to XVIII, and XVIII to XVII are exemplified in Belgian Patent Serial No. 747,348, Sept. 14, 1970, in the case wherein A is trimethylene. Those procedures are used when A is other than trimethylene and within the scope of A as defined above.

The transformation of alkylation product XVI to primary alcohol XXII (Chart B) is carried out by acid catalyzed hydrolysis of the tetrahydropyranyl ether XVI. Such hydrolysis of tetrahydropyranyl ethers is well known to those skilled in the art. Oxalic acid is especially preferred for this acid hydrolysis of XVI to XXII.

The oxidation of primary alcohols XXII to carboxylic acid XXIII (Chart B, R$_1$ = H) is carried out by oxidizing XXII with any oxidizing agent which will not also attack the acetylenic linkage in XXII. An especially useful reagent for this purpose is the Jones reagent, i.e., acidic chromic acid. See J. Chem. Soc. 39 (1946). Acetone is a suitable diluent for this purpose, and a slight excess of oxidant and temperatures at least as low as about 0°C., preferably about —10° to about —20°C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Soc. 87, 5661 (1965).

The acid thus formed (compound XXIII, R$_1$ = H) can then be esterified by procedures already known in the art for transforming carboxylic acids to esters. For example, a diazohydrocarbon, e.g., diazomethane, advantageously in diethyl ether solution, is reacted with the acid to produce the ester, e.g., the methyl ester, by known procedures. When $R_1$ is ethyl substituted with 3-chloro, 2 or 3 bromo, or 1, 2, or 3 iodo, the acid is reacted with the appropriate haloethanol, e.g., $\beta,\beta,\beta$-trichloroethanol, in the presence of a carbodiimide, e.g., dicyclohexylcarbodiimide, and a base, e.g., pyridine. This mixture, advantageously with an inert diluent, e.g., dichloromethane, usually produces the desired haloethyl ester within several hours at about 25°C. The other esters within the scope of $R_1$ are prepared by procedures known in the art.

In step 6 the vicinal hydroxy group of the glycol XXIV are modified by replacing the hydrogens with an alkanesulfonyl leaving-group, L, for example mesyl, containing up to and including 5 carbon atoms. Thus, the bis-alkanesulfonic acid esters XXV (Chart B) are prepared by reacting glycol XXIV with an alkylsulfonyl chloride or bromide, or with an alkanesulfonic acid anhydride. Alkylsulfonyl chlorides are preferred for this reaction. The reaction is carried out in the presence of a base to neutralize the by-product acid. Especially suitable bases are tertiary amines, e.g., dimethylaniline or pyridine. It is usually sufficient merely to mix the two reactants and the base, and maintain the mixture in the range 0° to 25° C. for several hours. The formula XXV bis-alkanesulfonic acid esters are then isolated by procedures known to the art.

The transformation in Chart D; Step 7a, of the modified glycol XXV to VIIId is carried out by reacting XXV with water in the range about 0° to about 60° C. The resulting product is racemic 5,6,17,18-dehydro-PGE$_3$ or an analog thereof. In making racemic 5,6,17,18-dehydro-PGE$_3$, usually 25° C. is a suitable reaction temperature, the reaction then proceeding to completion in about 5 to 10 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of formula VIIId isomers which differ in the configuration of the side chain hydroxy, that being either R or S. These are separated from by-products and from each other by silica gel chromatography. A usual by-product is the mono-sulfonic acid ester of formula XXVI (Chart D). This mono-sulfonic acid ester is esterified to the formula XXV bis-sulfonic acid ester in the same manner described above for the transformation of glycol XXIV to bis-ester XXV, and this is recycled in step 7a.

For the transformation of bis-esters XXV to the formula VIIId products, it is preferred to use the bis-methyl esters, i.e., compounds XXV wherein L is mesyl.

In step 8a the acetylenic linkages are hydrogenated to olefinic linkages. A suitable method is to hydrogenate over a Lindlar catalyst in the presence of quinoline. The Lindlar catalyst is 5% palladium-on-barium sulfate. Methanol or like inert solvent or diluent is used and the pressure is low, advantageously slightly above atmospheric and ordinarily not above about two atmospheres. The resulting products can be isolated by silica gel chromatography. If the starting material contains both the R and S epimers, the product VIIIe will also contain the R and S epimers. These also can be separated by silica gel chromatography. As shown on Chart D, the hydrogenation of VIIId (or Xd) leads to PG$_3$-type compounds depending on whether the acetylenic bonds of VIIId (or Xd) are reduced to cis-CH=CH—. The above described hydrogenation gives this type of reduction of the acetylenic bonds.

The transformation of the protected glycols XXV (Step 7b) to 5,6,17,18-dehydro-PGA$_3$-type compounds (Xd) is carried out by heating the formula XXV bis-ester in the range 40° to 100° C. with a combination of water, a base characterized by its water solution having pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for step 7a and hydrogenated as in step 8a. The same mono-sulfonic acid esters XXVI observed as by-products in step 7a are also observed in step 7b. Also, as in step 7b the bis-mesyl esters XXV are preferred. Also as in steps 7a and 8a, during production of Xd and Xe, alpha XXV given alpha Xd and alpha Xe, beta XXV gives beta Xd and beta Xe, and in each case, alpha and beta Xd and Xe, a mixture of R and S isomers is obtained. These R and S isomer mixtures are separated by silica gel chromatography.

The configuration of the —CH$_2$—C≡C—A—COOR$_1$ moiety does not change during these transformations of Charts B and D. Also the configuration does not change in hydrogenation. Therefore, when the —CH$_2$C≡C—A—COOR$_1$ is attached initially in alpha configuration racemic 5,6,17,18-dehydro-PGE$_3$-type, VIIId, PGE$_3$-type, VIIIe, 5,6,17,18-dehydro-PGA$_3$-type, Xd, and PGA$_3$-type, Xe, compounds are obtained, and when the moiety is attached in beta configuration, the 8-isoforms are obtained.

Resolution of the final product racemates or the racemic intermediates are carried out by procedures known in the art. For example, when a final compound of formula VIIIe, IXe, Xe, or XIe is a free acid, the dl form (racemate) thereof is resolved into the d and l forms (the natural and unnatural configurations) by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula VIII to XI is then obtained by treatment of the salt with an acid by known general procedures. Alternatively, the free acid form of the intermediate dehydro compounds VIIId, IXd, Xd, or XId is resolved into separate d and l forms and then esterified and transformed further to the corresponding optically active form of the final product VIIIe to XIe as described above.

Alternatively, glycol reactant XXIV, in exo or endo form, is transformed to a ketal with an optically active 1,2-glycol, e.g., D-(—) -2,3-butanediol, by reaction of said 1,2-glycol with the formula XXIV compound in the presence of a strong acid, e.g., p-toluenesulfonic acid. The resulting ketal is a mixture of diastereoisomers which is separated into the d and l diastereoisomers, each of which is then hydrolyzed with an acid, e.g., oxalic acid, to the original keto compound, now in optically active form. These reactions involving optically active glycols for resolution purposes are generally known in the art. See, for example, Chem. Ind. 1664 (1961) and J. Am. Chem. Soc. 84, 2938 (1962). Dithiols may be used instead of glycols.

The novel $PGE_3$, $PGF_3$, $PGA_3$, and $PGB_3$-type compounds of formula VIIIe to XIe wherein $R_3$ is alkyl of one to 4 carbon atoms, inclusive, preferably methyl or ethyl, are preferred over the corresponding $PGE_3$, $PGF_3$, $PGA_3$, and $PGB_3$-type compounds in which $R_3$ is hydrogen for the above-described pharmacological purposes. For convenience the compounds of the invention where $R_3$ is alkyl will be referred to as 15-alkyl analogs even through the number actually will be greater or less than 15 depending on whether the number of methylene groups in A is greater or less than three.

These 15-alkyl prostaglandin analogs are surprisingly and unexpectedly more useful than the corresponding 15-hydrogen compounds for the reason that they are substantially more specific with regard to potency in causing prostaglandin-like biological responses, and have a substantially longer duration of biological activity. For that reason, fewer and smaller doses of these 15-alkyl prostaglandin analogs are needed to attain the desired pharmacological results.

Although the above-mentioned 15-alkyl compounds are produced by the methods outlined above in Charts A–D, the preferred methods are set forth in Charts E and F as follows.

CHART E

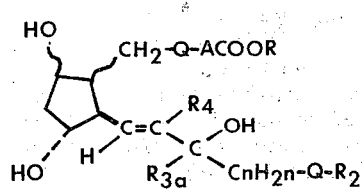

(Oxidation)

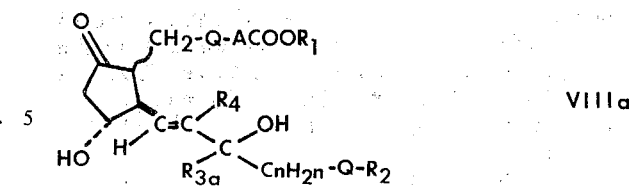

CHART F

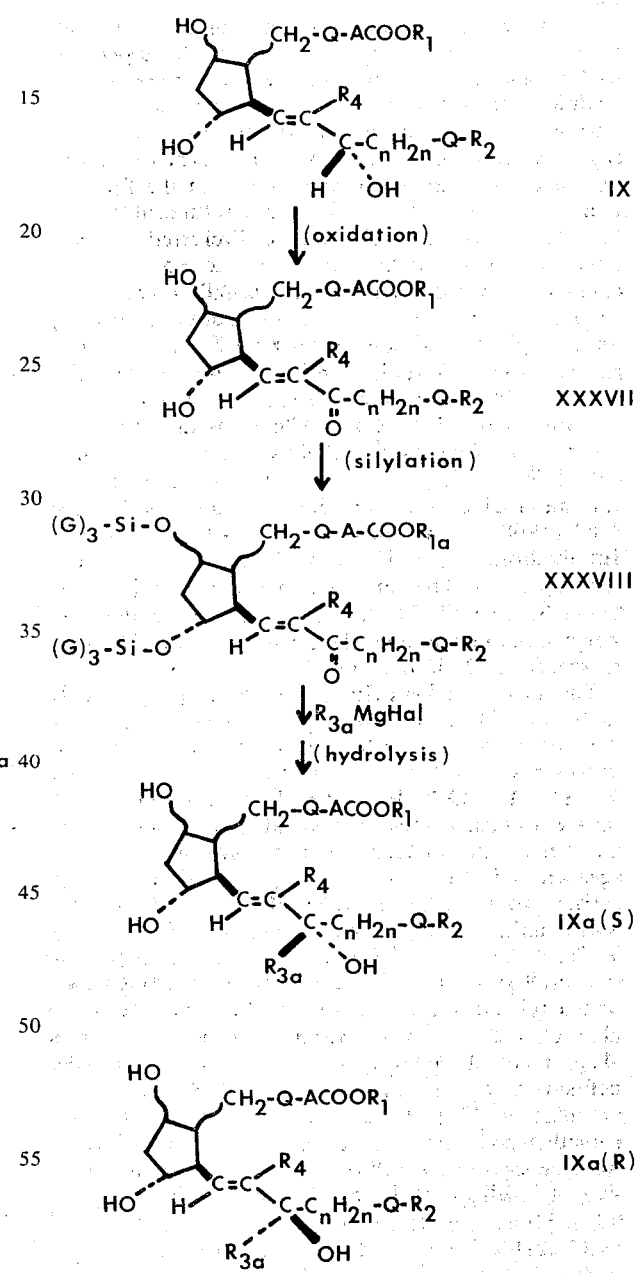

In Chart E is shown the transformation of 15-alkyl PGF-type acids and alkyl esters to the corresponding S PGE-type acids and alkyl esters by oxidation. For this purpose, an oxidizing agent is used which selectively oxidizes secondary hydroxy groups to carbonyl groups in the presence of carbon-carbon double bonds. Formula IXa is Chart E includes optically active compounds as shown and racemic compounds of that formula and the mirror images thereof, and also the 15-epimers of both of those, i.e., wherein the configuration at C-15 is R rather than S as shown. Also in Chart E, A, $R_1$, $R_2$, and $R_4$ are as defined above, $R_3a$ is alkyl of one to 4 carbon atoms, and both Q's are ethynylene or cisethylene.

For the transformations of Chart E, the β-hydroxy isomers of reactant IXa are suitable starting materials when the carboxyl side chain is alpha, although the corresponding α-hydroxy isomers are also useful for this purpose.

Oxidation reagents useful for the transformation set forth in Chart E are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize one of the secondary hydroxy groups of the formula IXa reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the formula VIIIa PGE-type product is isolated by conventional methods.

Examples of other oxidation reagents useful for the Chart E transformations are silver carbonate on diatomite [Chem. Commun. 1102 (1969)], mixtures of chromium trioxide and pyridine [Tetrahedron Letters 3363 (1968, J. Am Chem. Soc. 75, 422 (1953), and Tetrahedron, 18, 1351 (1962)], mixtures of sulfur trioxide in pyridine and dimethyl sulfoxide [J. Am. Chem. Soc. 89, 5505 (1967)], and mixtures of dicyclohexylcarbodiimide and dimethyl sulfoxide [J. Am. Chem. Soc. 87, 5661 (1965)].

The novel 15-alkyl $PGF_{3\alpha}$ - and $PGF_{3\beta}$ -type acids and esters of formula IXa are preferably prepared from the corresponding 15-hydrogen compounds by the sequence of transformations shown in Chart F, wherein formulas IX, XXXVII, XXXVIII, IXa(S), and IXa(R) include optically active compounds as shown and racemic compounds of those formulas and the mirror images thereof. Also in Chart F, $R_{3a}$ is alkyl of one to 4 carbon atoms, inclusive, and A, $R_1$, $R_2$, $R_4$ are as heretofore defined and Q is ethynylene or cisethylene. Also in Chart F, G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{1a}$ is alkyl or silyl of the formula —Si—$(G)_3$ wherein G is as defined above. The various G's of a —$Si(G)_3$ moiety are alike or different. For example, a —$Si(G)_3$ can be trimethylisilyl, dimethylphenylsilyl, or methylphenylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

In Chart F, the final $PGF_{3\alpha}$ and $PGF_{3\beta}$ -type products are those encompassed by formulas IXa(S) and IXa(R), respectively, where both Q's are cis-ethylene.

The heretofore-described acids and esters of formula IX are transformed to the corresponding intermediate 15-oxo acids and esters of formula XXXVII, by oxidation with reagents such as 2,3-dichloro-5,6-dicyano-1,4-benzoquinone, activated manganese dioxide, or nickel peroxide (see Fieser et al., "Reagents for Organic Synthesis," John Wiley & Sons, Inc., New York, N.Y., pp. 215, 637, and 731). Alternatively. these oxidations are carried out by oxygenation in the presence of the 15-hydroxyprostaglandin dehydrogenase of swine ling [see Arkiv for Kemi 25, 293 (1966)]These reagents are used according to procedures known in the art. See, for example, J. Biol. Chem. 239, 4097 (1964).

The novel 5,6,17,18-dehydro-$PGF_3$-type compounds of formula IXa are obtained by the borohydride reduction of the corresponding 5,6,17,18-dehydro-$PGE_3$-type compounds of formula VIIIa. Here again the numbering is merely typical and will vary according to the values of A and n.

Referring again to Chart F, the intermediate compounds of formula XXXVII are transformed to silyl derivatives of formula XXXVIII by procedures known in the art. See, for example, Pierce, "Silylation of Organic Compounds," Pierce Chemical Co., Rockford, Ill. (1968). Both hydroxy groups of the formula XXXVII reactants are thereby transformed to —O—Si—$(G)_3$ moieties wherein G is as defined above, and sufficient of the silylating agent is used for that purpose according to known procedures. When $R_1$ is the formula XXXVII intermediate is hydrogen, the —COOH moiety thereby defined is simultaneously transformed to —COO —Si—$(G)_3$, additional silylating agent being used for this purpose. This latter transformation is aided by excess silylating agent and prolonged treatment. When $R_1$ in formula XXXVII is alkyl, then $R_{1a}$ in formula XXXVIII will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

Referring again to Chart F the intermediate silyl compounds of the formula XXXVIII are transformed to the final compounds of formulas IXa(S) and IXa(R) by first reacting the silyl compound with a Grignard reagent of the formula $R_{3a}MgHal$ wherein $R_{3a}$ is as defined above, and Hal is chloro, bromo, or iodo. For this purpose, it is preferred that Hal be bromo. This reaction is carried out by the usual procedure for Gringnard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-S and 15-R isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-S and 15-R isomers are more readily separated by silica gel chromatography than are the corresponding acids. In those cases, it is advantageous to esterify the mixture of acids; separate the two esters, and then, if desired, saponify the esters by procedures known in the art and described herein.

The novel 15-alkyl PGA-type acids and esters of formula Xa are prepared from the 15-alkyl PGE compounds, VIIIa, heretofore described, by dehydration as shown in Chart G. For this purpose, a dehydrating agent is used which removes the hydroxy group from the alicyclic ring in the presence of a hydroxy group on a teritary carbon atoms. Formula VIIIa includes optically active compounds as shown and racemic compounds of that formula and the mirror images thereof, and also the 15-epimers of both of those, i.e., wherein the configuration at C-15 is R or S and that of the carboxyl side chain is $\alpha$ or $\beta$.

a carbodiimide and a catalytic amount of a copper (II) salt. Especially preferred are mixtures of at least an equivalent amount of dicyclohexylcarbodiimide and a catalytic amount of copper (II) chloride. An equivalent amount of a carbodiimide means one mole of the carbodiimide for each mole of the Formula-VIIIa reactant. To ensure completeness of the reaction, it is advantageous to use an excess of the carbodiimide, i.e., 1.5 to 5 or even more equivalents of the carbodiimide.

The dehydration is advantageously carried out in the presence of an inert organic diluent which gives a homogeneous reaction mixture with respect to the Formula-VIIIa reactant and the carbodiimide. Diethyl ether is a suitable diluent.

It is advantageous to carry out the dehyrdation in an atmosphere of an inert gas, e.g., nitrogen, helium, or argon.

CHART G

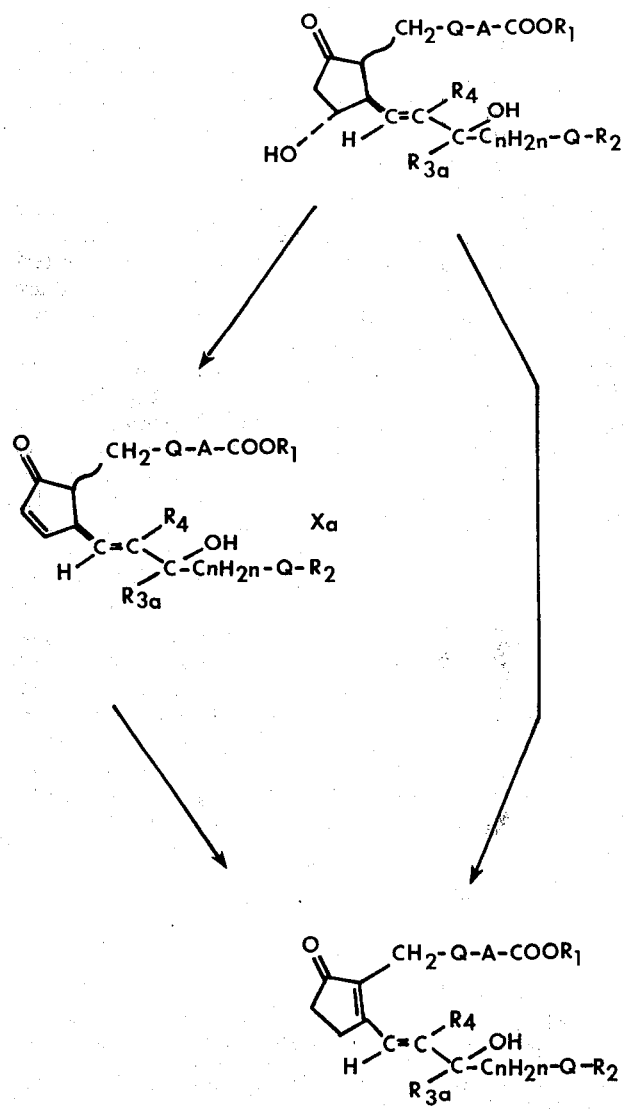

Dehydration agents useful for the transformation to PGA$_3$-type compounds set forth in Chart G are known in the art. Any of the known substantially neutral dehydrating agents is used for these reactions. See Fieser et al., "Reagents for Organic Syntheses", John Wiley & Sons, Inc., New York, 1967. Preferred dehydrating agents are mixtures of at least an equivalent amount of The time required for the dehydration will depend in part on the reaction temperature. With the reaction temperature in the range 20° to 30° C., the dehydration usually takes place in about 40 to 60 hours.

The Formula-Xa product is isolated by methods known in the art, e.g., filtration of the reaction mixture and evaporation of the filtrate. The product is then purified by methods known in the art, advantageously by chromatography on silica gel.

The conversion of Formula-VIIIa and Formula-Xa compounds to Formula XIa compounds is effected with base as described above in connection with Charts A and A-1.

The formula VIII and X compounds produced according to the processes outlined in Charts B, C, and D and discussed above are all carboxylic acid esters, wherein $R_1$ is not hydrogen. Moreover, when these compounds are used to produce compounds of formulas IX and XI according to the processes outlined in Chart A and discussed above, corresponding $R_1$ esters are likely to be produced, especially in the case of the PGF$_3$ compounds of formulas IX. For some of the uses described above, it is preferred that these formula VIII to XI compounds be in free acid form, or in salt form which requires the free acid as a starting material. It is also sometimes desirable to have the free acid or salt forms of the acetylenic compounds of the 5,6,17,18-dehydro-PGE$_3$-type (VIId) and the 5,6,17,18-dehydro-PGA$_3$-type (Xd) compounds, as well as the 5,6,17,18-dehydro-PGF$_3$-type (IXd) and 5,6,17,18-dehydro-PGB$_3$-type (XId) compounds and which are derivable therefrom by the processes outlined in Chart A-1, because these free acids and salt forms have properties like those of the corresponding hydrogenated (olefinic) compounds and are useful for the same purposes detailed above.

The formula IXe, XIe, and IXd, and XId $R_1$-esters are easily hydrolyzed or saponified by the usual known procedures, especially when $R_1$ is alkyl of one to 4 carbon atoms, inclusive. Therefore it is preferred when the free acid form of compounds IXe, XIe, IXd, and XId is desired, that $R_1$ by such alkyl, especially methyl or ethyl.

On the other hand, the formula VIIIe, Xe, VIIId, and Xd products are difficult to hydrolyze or saponify without unwanted structural changes in the desired acids. There are two other procedures useful to make the free acid form of formula VIIIe, Xe, VIIId, and Xd products.

One of those procedures is applicable mainly in preparing the free acids from the corresponding alkyl esters wherein the alkyl group contains one to 8 carbon atoms, inclusive. That procedure comprises subjecting the alkyl ester corresponding to formula VIIIe, Xe, VIIId, or Xd to the acylase enzyme system of a microorganism species of Subphylum 2 of Phylum III, and thereafter isolating the acid. Especially preferred for this purpose are species of the orders Mucorales, Hypocreales, Moniliales, and Actinomycetales. Also especially preferred for this purpose are the species of the families Mucoraceae, Cunninghamellaceae, Nectreaceae, Moniliaceae, Dematiaceae, Tuberculariaceae, Actinomycetaceae, and Streptomycetaceae. Also especially preferred for this purpose are species of the genera Absidia, Circinella, Gongronella, Rhizopus, Cunninghamella, Calonectria, Aspergillus, Penicillium, Sporotrichum, Cladosporium, Fusarium, Nocardia, and Streptomyces.

Examples of microorganisms falling within the scope of those preferred orders, families, and genera are listed in U.S. Pat. No. 3,290,226 and details of the process are disclosed in German Offenlegunsschift No. 1,937,678, reprinted in Farmdoc Complete Specifications, Book No. 13, No. 6863R, Week R5, Mar. 18, 1970.

This enzymatic ester hydrolysis is carried out by shaking the formula VIIIe, Xe, VIIId, or Xd alkyl ester in aqueous suspension with the enzyme contained in a culture of one of the above-mentioned microorganism species until the ester is hydrolzyed. A reaction temperature in the range 20° to 30° C. is usually satisfactory. A reaction time of one to 20 hours is usually sufficient to obtain the desired hydrolysis. Exclusion of air from the reaction mixture, for example, with argon or nitrogen is usually desirable.

The enzyme is obtained by harvest of cells from the culture, followed by washing and resuspension of the cells in water, and cell disintegration, for example, by stirring with glass beads or by sonic or ultrasonic vibrations. The entire aqueous disintegration mixture is used as a source of the enzyme. Alternatively and preferably, however, the cellular debris is removed by centrifugation or filtration, and the aqueous supernatant or filtrate is used.

In some cases, it is advantageous to grow the microorganism culture in the presence of an alkyl ester of an aliphatic acid, said acid containing 10 to 20 carbon atoms, inclusive, and said alkyl containing one to 8 carbon atoms, inclusive, or to add such an ester to the culture and maintain the culture without additional growth for one to 24 hours before cell harvest. Thereby, the enzyme produced is sometimes made more effective in transforming the formula VIIIe, Xe, VIIId, or Xd ester to the free acid. An example of a useful alkyl ester for this purpose is methyl oleate.

Although, as mentioned above, most of the $R_1$ esters encompassed by formulas VIIIe, Xe, VIIId, and Xd are not easily hydrolyzed or saponified to the corresponding free acids, certain of those esters are transformed to free acids by another method. Those esters are the haloethyl esters wherein $R_1$ is $-CH_2CCl_3$. They are transformed to free acids by treatment with zinc metal and an alkanoic acid of 2 to 6 carbon atoms, preferably acetic acid. Zinc dust is preferred as the physical form of the zinc. Mixing the halo ethyl ester with the zinc dust at about 25° C. for several hours usually causes substantially complete replacement of the haloethyl moiety of the formula VIIIe, Xe, VIIId, or Xd ester with hydrogen. The free aicd is then isolated from the reaction mixture by procedures known to the art. This procedure is also applicable to the production of the free acid form of the formula IXe, XIe, IXd, and XId compounds from the corresponding haloethyl esters thereof.

As described above, the alkylation of cyclic ketone XV to ketone XXIII (Chart B) usually produces a mixture of alpha and beta alkylation products with respect to the $-CH_2-C \equiv C-A-COOR_1$ or the

moiety.

Also as described above, those two isomers lead to different final products, alpha leading to the PG$_3$-series and beta leading to the 8-iso-PG$_3$-series. If a compound in one or the other of those series is preferred, there are two methods for favoring production of the preferred final product.

One of those methods involves isomerization of the final product of formula VIIIe or formula VIIId. Either the alpha isomer of formula VIIIe or VIIId, or the beta isomer of formula VIIIe or VIIId is maintained in an inert liquid diluent in the range 0° to 80° C. and in the presence of a base characterized by its water solution having a pH below about 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° C. takes about one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner, by repeated isomerizations and separations, substantially all of the less preferred isomer of the formula VIIIe of formula VIIId compound is transformed to more preferred isomer.

The second method for favoring production of a preferred final formula VIIIe or formula VIIId isomer involves any one of the intermediates of formulas XVI, XXII, XXIII, XXIV, or XXV' (Chart B). Either the alpha form or the beta form of one of those intermediates is transformed to a mixture of both isomers by maintaining one or the other isomer, alpha, or beta, in an inert liquid diluent in the presence of a base and in range 0° to 100° C. until a substantial amount of the starting isomer has been isomerized to the other isomer. Preferred bases for this isomerization are alkali metal amides, alkali metal alkoxides, alkali metal hydrides, and triarylmethyl alkali metals. Especially preferred are alkali metal tert-alkoxides of 4 to 8 carbon atoms, e.g., potassium tert-butoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromatography. The less preferred isomer is then subjected to the same isomerization to produce more of the preferred isomer. In this manner, by repeated isomerizations and separations, substantially all of the less preferred isomer of any of these intermediates is transformed to the more preferred isomer.

The final formula VIIIe, IXe, XE, and XIe compounds and VIIId, IXd, Xd, and XId compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIIIe, IXe, Xe, XIe, VIIId, IXd, Xd, or XId acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIIIe, IXe, VIIId, IXd, Xd, or XId acid with the stoichiometric amount of the corresponding quaternary ammonium hydroxide in water solution, followed by evaporation of the water.

The invention can be more fully understood by the following examples and preparations in which the parts are by weight and solvent ratios are by volume unless otherwise specified.

All temperatures are in degrees centigrade.

NMR spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

For convenience the formulas are given in the natural configuration, it being understood, though, that the compounds produced, unless otherwise specified, include the enantiomorphs.

EXAMPLE 1

Racemic $PGE_3$ methylester (XXXIX)

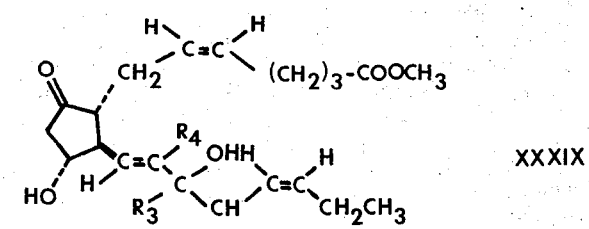

XXXIX

Part A-1 Endo-bicyclo[3.1.0]hexan-3-ol-6-carboxylic acid methyl ester

A mixture of endo-bicyclo[3.1.0]nex-2-ene-6-carboxylic acid methyl ester (103 g.) and anhydrous diethyl ether (650 ml.) is stirred under nitrogen and cooled to −5° C. A one molar solution (284 ml.) of diborane in tetrahydrofuran is added dropwise during 30 minutes while keeping the temperature below 0° C.

The resulting mixture is then stirred and allowed to warm to 25° C. during 3 hours. Evaporation under reduced pressure gives a residue which is dissolved in 650 ml. of anhydrous diethyl ether. The solution is cooled to 0° C., and 3 normal aqueous sodium hydroxide solution (172 ml.) is added dropwise under nitrogen and with vigorous stirring during 15 minutes, keeping the temperature at 0° to 5° C. Next, 30% aqueous hydrogen peroxide (94 ml.) is added dropwise with stirring during 30 minutes at 0° to 5° C. Then, 500 ml. of saturated aqueous sodium chloride solution is added, and the diethyl ether layer is separated. The aqueous layer is washed with four 200 ml. portions of ethyl acetate, the washings being added to the diethyl ether layer, which is then washed with saturated aqueous sodium chloride solution, dried, and evaporated to give 115 g. of a residue. This residue is distilled under reduced pressure to give 69 g. of a mixture of the methyl esters of endo-bicyclo[3.1.0]hexan-3-ol-6-carboxylic acid and endo-bicyclo[3.1.0]hexan-2-ol-6-carboxylic acid; b.p. 86°–95° C. at 0.5 mm.

Part A-2 Endo-bicyclo[3.1.0]hexan-3-ol-6-carboxylic acid methyl ester tetrahydropyranyl ether The 2-ol and 3-ol mixture (66 g.) obtained according to Part A-1 in 66 ml. of dihydropyran is stirred and cooled at 15°–20° C. during addition of 3 ml. of anhydrous diethyl ether saturated with hydrogen chloride. The temperature of the mixture is then kept in the range 20° to 30° C. for one hour with cooling, and is then kept at 25° for 15 hours. Evaporation gives a residue which is distilled under reduced pressure to give 66 g. of a mixture of the methyl esters-tetrahydropyranyl ethers of endobicyclo[3.1.0]hexan-3-ol-6-carboxylic acid and endobicyclo[3.1.0]hexan-2-ol-6-carboxylic acid; b.p. 96°–104° C. at 0.1 mm.

Part A-3
Endo-6-hydroxymethylbicyclo[3.1.0]hexan-3-ol-3-tetrahydropyranyl ether

A solution of the mixture (69 g.) of products obtained according to Part A-2 in 300 ml. of anhydrous diethyl ether is added dropwise during 45 minutes to a stirred and cooled mixture of lithium aluminum hydride (21 g.) in 1300 ml. of anhydrous diethyl ether under nitroge. The resulting mixture is stirred 2 hours at 25° C., and is then cooled to 0° C. Ethyl acetate (71 ml.) is added, and the mixture is stirred 15 minutes. Water (235 ml.) is then added, and the diethyl ether layer is separated. The water layer is washed twice with diethyl ether and twice with ethyl acetate. A solution of Rochelle salts is added to the aqueous layer, which is then saturated with sodium chloride and extracted twice with ethyl acetate. All diethyl ether and ethyl acetate solutions are combined, washed with saturated aqueous sodium chloride solution, dried, and evaporated to give 61 g. of a mixture of the 3-tetrahydropyranyl ethers of endo-6-hydroxymethylbicicyl-[3.1.0]hexan-3-ol and endo-6-hydroxymethylvicyclo[3.1.0]-hexan-2-ol.

Part A-4
Endo-bicyclo[3.1.0]hexan-3-ol-6-carboxaldehyde 3-tetrahydropyranyl ether A solution of the mixture (34 g.) of products obtained according to Part A-3 in 1000 ml. of acetone is cooled to −10° C. Jones reagent (75 ml. of a solution of 21 g. of chromic anhydride, 60 ml. of water, and 17 ml. of concentrated sulfuric acid), precooled to 0° C., is added dropwise with stirring during 10 minutes at −10° C. After 10 minutes of additional stirring at −10° C., isopropyl alcohol (35 ml.) is added during 5 minutes, and stirring is continued for 10 minutes. The reaction mixture is then poured into 8 l. of an ice and water mixture. The resulting mixture is extracted 6 times with dichloromethane. The combined extracts are washed with aqueous sodium bicarbonate solution, dried, and evaporated to give 27 g. of a mixture of the tetrahydropyranyl ethers of endo-bicyclo[3.1.0]hexan-3-ol-6-carboxaldehyde (XL) and endo-bicyclo[3.1.0]hexan-2-ol-6-carboxaldehyde.

Part B 3-Hexynyl-1-triphenylphosphonium bromide

To a solution of 130 g. (0.81 moles) of 1-bromo-hex-3-yne in 250 ml. of benzene is added 236 g. of (0.9 moles) of triphenylphosphine. The resulting solution is heated with stirring in a heating bath of 80° C. for 24 hours. Stirring is continued at room temperature for 24 hours, then the reaction mixture is allowed to stand for 48 hours. An oil precipitated. The supernatant solution is decanted, the oil stirred in 200 ml. of benzene. The oil is again allowed to separate and the supernatant solution separated. The oil is dried under vacuum at room temperature, the oil solidifies while drying. The decanted solutions are combined and heated at 80° C. bath temperature for 48 hours, workup as above resulted in a second batch of solid material making a total yield of 210 g. of 3-hexynyl-1-triphenylphosphonium bromide.

Part C
Endo-6-Hept-1-en-4-ynyl-bicyclo[3.1.0]hexan-3-ol-3-tetrahydropyranyl ether (XLI)

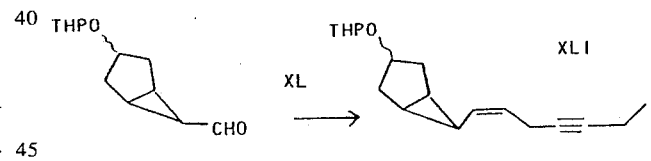

105 g. of the phosphonium salt of Part B is stirred in 1200 ml. of dry tetrahydrofuran under a nitrogen atmosphere. The reaction flask is cooled in an ice-methanol bath. 150 ml. of a 15.1% hexane solution of n-butyl lithium is added dropwise. When the addition was complete, stirring is continued for 20 minutes. Then a solution of 42 g. of aldehyde XL in 150 ml. tetrahydrofuran is added dropwise with stirring over a period of 15 minutes.

The ice-methanol bath is replaced by a heating bath and the reaction mixture is heated at 60°–70° c. bath temperature for 3 hours. The reaction mixture is allowed to stand at room temperature overnight. The solvent is removed under reduced pressure. The residue is treated with 500 ml. benzene and filtered; the solid is washed with 500 ml. benzene, the benzene solutions combined and evaporated under reduced pressure. The resulting oil is triturated with 500 ml. of Skellysolve B (technical hexane), filtered and the resulting solution evaporated under reduced pressure to give 37 g. of a yellow oil. The oil is chromatographed using 1500 g. of silica gel. The column is developed with seven 1500 ml. portions of 1:1 benzene-Skellysolve "B", seven 1500 ml. portions of benzene, five 1500 ml. portions of benzene containing 5% ethyl acetate, five 1500 ml. portions of benzene containing 10% ethyl acetate, and three 1500 ml. portions of ethyl acetate. Fractions 12–18 are combined to give a total of 12.9 g. of tetrahydropyranyl-ether XLI as a colorless oil, fractions 19–26 are combined to give a total of 13.5 g. of the corresponding alcohol XLII as a colorless oil.

Part D
Endo-6-hept-1-en-4-ynyl-bicyclo[3.1.0]hexan-3-ol (XLII)

12.8 g. of tetrahydropyranylether XLI is dissolved in 300 ml. of methanol, 600 mg. of oxalic acid is added and the solution heated under reflux for 1.5 hours. The methanol is evaporated under reduced pressure, the resulting residue dissolved in 300 ml. of methylene chloride, washed with 100 ml. of saturated aqueous $HaHCO_3$ and dried over $Na_2SO_4$. Evaporation of solvent results in 11.2 g. of crude alcohol XLII. The alcohol is combined with alcohol XLII obtained in Part C and used for Part E without further purification.

Part E
Endo-6-hept-1-en-4-ynyl-bicyclo[3.1.0]hexan-3-one (XLIII)

A solution of 23.7 g. of alcohol XLII in 720 ml. of acetone is cooled to −5° to 31 10° C. 48 ml. of Jones reagent is added dropwise over a period of 15 minutes maintaining a reaction temperature of 0 to 5° C. When the addition is complete, stirring is continued for 10 minutes at −5° C. 24 ml. of isopropanol is added and stirring continued for 10 minutes. The green solution is poured into 5 liters of water and the aqueous solution extracted with five 1 liter portions of methylene chloride. The combined extracts are washed with 750 ml. of saturated aqueous $NaHCO_3$, two 750 ml. portions of saturated aqueous NaCl, and dried over $Na_2SO_4$. Evaporation of solvent under reduced pressure yields 18.2 g. of brown oil which is chromatographed using 800 g. of silica gel. The column is developed with four 800 ml. portions of Skellysolve B containing 2.5% ethyl acetate and twelve 800 ml. portions of Skellysolve B containing 5% ethyl acetate. Fractions 9–14 are combined to yield 5.3 g. of ketone XLII as a colorless oil.
NMR: 1 H at 5.4 – 5.9δ (multiplet), 1 H at 4.7 – 5.2δ (multiplet), 2 H at 2.75 – 3.0δ; 9 H at 1.4 – 2.75δ, 3 H at 0.9 – 1.36δ (triplet).

Part F
Endo-(6-hept-1-en-4-ynyl)-2-(6-carboxyhex-2-yn-α-yl)-bicyclo[3.1.0]hexan-3-one methyl ester (XLIVα)

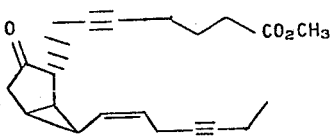

A solution of 8.1 g. of ketone XLIII and 34.4 g. of methyl 7-iodo-hept-5-ynoate in 300 ml. of dry tetrahydrofuran is stirred at room temperature under a nitrogen atmosphere. A solution of 7.16 g. of potassium t-butoxide and 6.67 g. of dicyclohexyl-18-crown-6 (Pedersen, J. Am. Chem. Soc. 89, 7017, 1967) in 450 ml. of dry tetrahydrofuran is added dropwise over a period of 1.5 hours. Stirring is continued for 10 minutes, then 75 ml. of 1N HCl is added followed by 900 ml. of saturated aqueous NaCl solution. The reaction mixture is extracted with three 750 ml. portions of ether, the extract washed with two 450 ml. portions of 5% aqueous $Na_2S_2O_3$ and 450 ml. of saturated aqueous NaCl solution, and dried over $Na_2SO_4$. The solvent is removed under reduced pressure to give 34 g. of a brown oil which is chromatographed using 1 kg. of silica gel. The column is developed with ten 1 liter portions of Skellysolve B containing 2.5% ethyl acetate, ten 1 liter portions of Skellysolve B containing 5% ethyl acetate, and ten 1 liter portions of Skellysolve B containing 10% ethyl acetate. Fractions 21–24 are combined to give 1.6 g. of keto-ester XLIVα as a colorless oil.
NMR: 2 H at 4.7 – 5.9δ (multiplet), 3 H at 3.63δ (singlet).
Mass spectrum: peaks at 326 (M+), 311 (m-15), 295 (m-31).

Part G
Endo-6-(1,2-dihydroxy-hept-4-ynyl)-2-(6-carboxyhex-2-yn-α-yl)bicyclo[3.1.0]hexan-3-one methyl ester (XLV)

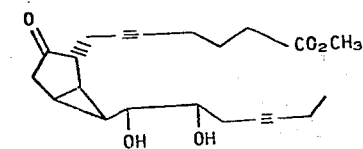

A solution of 1.47 g. of keto-ester XLIVα in 8 ml. of dry pyridine is stirred and cooled in an ice-methanol bath. 1.14 g. of osmium tetroxide is added and the reaction mixture allowed to stir in the melting ice-methanol bath overnight. A solution of 2 g. of $NaHSO_3$ in 30 ml. of water is added and stirring continued at room temperature for 2 hours. 250 ml. of ethyl acetate is added and the mixture dried over 60 g. of $Na_2SO_4$. Evaporation of solvent under reduced pressure yields 1.28 g. of a dark brown oil which is chromatographed using 125 g. of silica gel. The column is developed with eleven 125 ml. portions of a 1:1 mixture of ethyl acetate and Skellysolve. Fractions 4–11 are combined to yield 504 mg. of glycol XLV, a mixture of the recemates of two diastereoisomers, as a colorless oil.
NMR: no vinyl protons, only protons between 0.9 and 4.3δ, 3 H at 3.63δ (singlet), 3 H at 0.95 – 1.3δ (triplet).

The two diastereomeric racemates are separated by chromatography and the separated recemates resolved by the method of Corey et. al., J. Am. Chem. Soc. 84, 2938 (1962) which involves reacting this keto compound with optically active L(+)-2,3-butanedithiol in the presence of p-toluene sulfonic acid and separating the resulting diasteromeric ketals on a preparative chromatograph column and then by hydrolyzing the separated diasterisomers. There is thus obtained the d and the l forms of both diasteroisomers, making four enantiomorphs in all.

Part H Racemic 5,6,17,18-dehydro-PGE₃ methyl ester (XLVl,S) and its 15-epimer (XLVl,R)

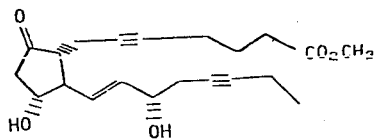

XLVI (S)

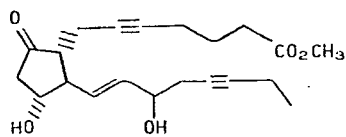

XLVI (R)

A solution of 650 mg. of glycol XLV in 20 ml. of dry pyridine is stirred under a nitrogen atmosphere in an ice bath. 2 ml. of methanesulfonylchloride is added, and the mixture stirred in the ice bath for 1.5 hours, then at room temperature for 1 hour. The mixture is cooled in an ice bath and diluted with 30 ml. of ice water, after stirring for 10 minutes the mixture is extracted with three 100 ml. portions of ethyl acetate. The extract is washed with 70 ml. ice cold 10% aqueous $H_2SO_4$, 70 ml. ice cole 10% aqueous $Na_2CO_3$ and two 70 ml. portions of ice cold saturated aqueous NaCl solution. The ethyl acetate solution is dried over $Na_2SO_4$. Evaporation of the solvent under reduced pressure yielded 870 mg. of brown oil which is dissolved in 20 ml. of acetone, 10 ml. of water is added and the solution allowed to stand at room temperature overnight. The acetone is removed under reduced pressure, the aqueous solution diluted with 25 ml. of water and extracted with three 75 ml. portions of ethyl acetate. The extract is washed with 50 ml. saturated aqueous $NaHCO_3$ and two 50 ml. portions of saturated aqueous NaCl. The ethyl acetate solution is dried over $Na_2SO_4$. Evaporation of the solvent under reduced pressure yields 580 mg. of a brown oil which is chromatographed using 65 g. of silica gel. The column is developed with six 60 ml. portions of Skellysolve B-ethyl acetate 3:1, five 60 ml. portions of Skellysolve B-ethyl acetate 1:1, five 60 ml. portions of Skellysolve B-ethyl acetate 1:3, five 60 ml. portions of ethyl acetate, and five 60 ml. portions of ethyl acetate containing 5% methanol. Fractions 17–23 are combined to yield 116 mg. of a colorless oil, mainly a mixture of XLVl(S) and XLVl(R). The oil is chromatographed using 12 g. silica gel. The column is developed with five 10 ml. portions each of ethyl acetate-Skellysolve B 60:40, ethyl acetate-Skellysolve B 70:30, ethyl acetate-Skellysolve B 8:20, ethyl acetate-Skellysolve B 90:10, B 90:10, ethyl acetate, and ethyl acetate containing 5% methanol. Fractions 9-12 are combined to yield 29 mg. of pure racemic 5,6,17,18-dehydro-15-epi-PGE₃ methylester, XLVl(R), as a colorless oil.

Mass spectrum: 342 (M-18); 329 (M-31); 324 (M-36); 293 (M-67); 274 (293-18).

Fractions 15–27 are combined to yield 60 mg. of a colorless oil containing XLVl(S) as the main product This oil is chromatographed using 10 g. of silica gel. The column is developed with twenty-eight 10 ml. portions of ethyl acetate-Skellysolve B 70:30 and nine 10 ml. portions of ethyl acetate. Fractions 13–21 combined to give 29 mg. of racemic 5,6,17,18-dehydro-PGE₃-methylester, XLVl(S), as a colorless oil, which is crystallized from ethyl acetate-Skellysolve B.
m.p. 94°–95° C.

Mass spectrum: 342 (M-18); 329 (M-31); 324 (M-36); 293 (M-67); 275 (293-18).

IR: 3420, 3330, 1730, 1340, 1245, 1230, 1160, 1080, 965.

By substituting the glycol XLIV by each of the four enantiomorphs of Part G, there are obtained the d and l forms of 5,6,17,18-dehydro-15-epi-PGE₃-methylester and the d and l forms of 5,6,17,18-dehydro-PGE₃ methylester.

Part 1 PGE₃ methylester

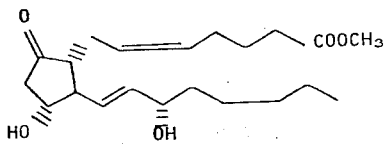

XLVII (S)

20 mg. of racemic 5,6,17,18-dehydro-PGE₃ Meth, lester, XLVI(S), are dissolved in 2 ml. methanol, 5 mg. of 5% palladium-on-barium sulfate and 2 drops of synthetic quninoline are added. The mixture is stirred and the hydrogenation performed at a slight positive hydrogen-pressure. The reaction is following by thin layer chromatography (silica gel, impregnated with silver nitrate; A IX system: ethyl acetate/acetic acid/2,2,4-trimethylpentane/water 90/20/50/100, organic layer); the reaction product is more polar and shows a lower $R_f$ value than the starting material. When the reaction is complete the mixture is filtered, the filtrate concentrated under reduced pressure and chromatographed using silica gel impregnated with silver nitrate. The column is developed with Skellysolve B containing increasing amounts of ethyl acetate. The fractions containing XLVII(S) are combined and the solvents evaporated under reduced pressure to yield racemic PGE₃ methylester (XLVII,S).

By substituting in part F the methyl 7-iodo-hept-5-ynoate by β,β,β-trichloroethyl 7-iodo-hept-5-ynoate, there are obtained in parts F, G, H, and I the corresponding β,β,β-trichloroethyl esters.

In part F a small amount of the 2-epimer, endo-6-(hept-1-en-4-ynyl)-2-(6-carboxyhex-2-yn-β-yl)bicyclo-[3.1.0]hexan-3-one methylester (XLIVβ), is formed. This can be isolated by chromatography and processes by the procedures of Parts G, H, and I to the corresponding 2-epimer in part G and the 8-iso PGE₃-types in parts H and I.

By substituting the racemic 5,6,17,18-dehydro-PGE₃ methyl ester by racemic 5,6,17,18-dehydro-15-epi-PGE₃ methylester or β,β,β-trichloroethylester and the 8-iso forms thereof, there are obtained racemic 15-epi-PGE₃ methylester, and racemic 15-epi-PGE₃ β,β,β-trichloroethylester and the 8-iso forms thereof. By substituting the above racemates by the d and l forms thereof, there are obtained d- and l-5,6,17,18-dehydro-PGE₃ methyl and β,β,β-trichloroethyl esters, d- and l-5,6,17,18-dehydro-15-epi-PGE$_3$ methyl and $\beta,\beta,\beta$-trichloroethyl esters and the 8-iso forms thereof.

EXAMPLE 2

Racemic PGE$_3$ (S).

Zinc dust (400 mg.) is added to a solution containing racemic PGE$_3$ $\beta,\beta,\beta$-trichloroethyl ester (100 mg.) in 5 ml. of a mixture of acetic acid and water (9:1 v/v). This mixture is stirred under nitrogen 2 hours at 25° C. Ethyl acetate (4 volumes) is then added, followed by addition of one normal hydrochloric acid (one volume). The ethyl acetate layer is separated, washed with water and then with saturated aqueous sodium chloride solution, dried, and evaporated. The residue is chromatographed on 15 g. of acid-washed silica gel (Silicar CC4), being eluted with 100 ml. of 50%, 100 ml. of 80%, and 200 ml. of 100% ethyl acetate in Skellysolve B, collecting 20-ml. fractions. Fractions 13–18 are combined and evaporated to give racemic PGE$_3$; same mobility as optically active PGE$_3$ and same color (with vanillin-phosphoric acid spray) on TLC silica gel and silver nitrate-impregnated silica gel plates; NMR peaks and infrared absorption (CH$_3$ Cl$_2$ solution) same as optically active PGE$_3$.

EXAMPLE 3

Racemic 15-epi-PGE$_3$ (R).

Following the procedure of Example 2, racemic 15epi-PGE$_3$ $\beta,\beta,\beta$-trichloroethyl ester is transformed to racemic 15-epi-PGE$_3$.

EXAMPLE 4

Racemic 5,6,17,18-dehydro-PGE$_3$ (S).

Following the procedure of Example 2, racemic 5,6,17,18-dehydro-PGE$_3$ $\beta,\beta,\beta$-trichloroethyl ester is transformed to racemic 5,6,17,18-dehydro-PGE$_3$.

EXAMPLE 5

Racemic 5,6,17,18-dehydro-15-epi-PGE$_3$ (R).

Following the procedure of Example 2, racemic 5,6,17,18-dehydro-15-epi-PGE$_3$ $\beta,\beta,\beta$-trichloroethyl ester is transformed to racemic 5,6,17,18-dehydro-15-epi-PGE$_3$.

The racemates of Examples 2, 3, 4, and 5 are resolved by forming the salt with brucine, separating the disasteroisomers on a preparative chromatographic column, neutralizing the separated diasteroisomers with hydrochloric acid and recovering the optically active isomer by extraction with ethyl acetate. There are thus obtained d- and l-PGE$_3$, d- and l-15-epi-PGE$_3$, d- and l-5,6,17,18-dehydro-PGE$_3$ and d- and l-5,6,17,18-dehydro-15-epi-PGE$_3$.

Following the above procedures, the beta isomers of the $\beta,\beta,\beta$-trichloroethyl esters of racemic PGE$_3$, racemic 15-epi-PGE$_3$, racemic 5,6,17,18-dehydro-PGE$_3$, and racemic 5,6.17,18-dehydro-5-epi-PGE$_3$ are each transformed on 8-iso-PGE$_3$, 8-iso-15-epi-PGE$_3$, 5,6,17,18-dehydro-8-iso-PGE$_3$, and 5,6,17,18-dehydro-8-iso-15-epi-PGE$_3$, respectively, in the d-, l- and racemic forms.

Also following the above procedures, each of $\beta,\beta,\beta$-trichloroethyl esters of the racemic PGE$_3$-type compounds and the racemic 15-epi-PGE$_3$-type compounds defined above is transformed to the corresponding racemic PGE$_3$-type acid and the racemic 15-epi-PGE$_3$-type acid, including the corresponding 8-iso acids, and the d- and l-forms thereof.

Also following the above procedures, each of the $\beta,\beta,\beta$-trichloroethyl esters of the racemic 5,6,17,18-dehydro-PGE$_3$-type compounds and the racemic 5,6,17,18-dehydro-15-epi-PGE$_3$-type compounds is transformed to the corresponding racimic 5,6,17,18-dehydro-PGE$_3$-type acid and the racemic 5,6,17,18-dehydro-15-epi-PGE$_3$-type acid, including the 8-iso acids, and the d- and l- forms thereof.

EXAMPLE 6

Racemic PGE$_3$.

Part A Enzyme preparation

A medium is prepared consisting of 2% corn steep liquor (a mixture of equal parts of cerelose and glucose) in tap water. This is brought to pH 4.5 by adding hydrochloric acid, and 1% of methyl oleate is added. Four 500 ml. flasks each containing 100 ml. of the above medium are inoculated with *Cladosporum resinae* (Cl-11, ATCC 11,274) and are placed on a shaker at room temperature (about 28° C.) for 4 days. The culture is then placed in 40 ml. centrifuge tubes and centrifuged at about 2000 rmp. in a clinical centrifuge. The liquid is decanted from the centrifuge tubes and the collected cells are washed with cold water. The washed cells from 2 centrifuge tubes are suspended in 50 ml. of ice cold 0.05 M pH 7.0 phosphate buffer and placed in small Waring blender cup chilled with ice. Glass beads are added and the suspended cells are churned in the blender for 15 minutes. The resulting suspension of broken cells is centrifuged in a clinical centrifuge at about 2000 r.p.m. for 15 minutes at room temperature, then the supernatant liquid is collected. This supernatant liquid contains Cladosporium resinae acylase and is used directly for the hydrolysis of PG$_3$-type alkyl esters or is stored, preferably frozen, until needed.

Part B Esterase hydrolysis of racemic PGE$_3$ methyl ester

Ten milliliters of the supernatant liquid containing Cladosporium resinae acylase, prepared as described in Part A of this example and 50 mg. of racemic PGE$_3$ methyl ester are shaken at room temperature under nitrogen for about 19 hours, then 70 ml. of acetone is added and the mixture is filtered giving a filtrate and an insoluble residue. The filtrate is evaporated under reduced pressure and gives 40–50 mg. of a slightly yellow oil comprising racemic PGE$_3$. Both this oil and the insoluble residue are combined and chromatographed over 10 g. of acid washed silica gel (Silic ARCC-4, Mallinckrodt). Elution is with Skellyvolve B containing increasing amounts of ethyl acetate, collecting 50 ml. fractions as follows:

| Fraction | Solvent | | | |
|---|---|---|---|---|
| 1 | Skellysolve B | | | |
| 2 | 40 ml | Skellysolve B | 10 ml. | ethyl acetate |
| 3 | 30 | " | 20 | " |
| 4 | 25 | " | 25 | " |
| 5 | 20 | " | 30 | " |
| 6 | 10 | " | 40 | " |
| 7 | 5 | " | 45 | " |
| 8 | ethyl acetate | | | |
| 9 | " | | | |
| 10 | " | | | |
| 11 | " | | | |
| 12 | 100 ml. of ethyl acetate | | | |

Fractions 6 to 12 are combined and evaporated to give racemic PGE$_3$.

Following the procedure of Example 5, each of the methyl esters of the PGE$_3$-type and 5,6,17,18-dehydro-PGE$_3$-type compounds defined above (racemates, optically active forms and 8- and 15-position epimers) are enzymatically hydrolyzed to the corresponding free acid.

Also following the procedure of Example 5, each of the methyl esters of the PGF$_3$-type, PGA$_3$-type, PGB$_3$-type and the corresponding 5,6,17,18-dehydro-PG$_3$-type compounds (racemates, optically active forms and 8- and 15-position epimers) is enzymatically hydrozyled to the corresponding free acid.

EXAMPLE 7

Racemic PGF$_{3\alpha}$ and racemic PGF$_{3\beta}$

A solution of sodium borohydride (70 mg.) in 5 ml. of ice-cold methanol is added dropwise with stirring to a solution of racemic PGE$_3$ (22 mg.) in 1.5 ml. of methanol at 0° C. This mixture is stirred at 0° C. for 30 minutes, and is then stirred and allowed to warm to 25° C. during one hour. After evaporation, water (10 ml.) is added, and the mixture is acidified with one normal hydrochloric acid, saturated with sodium chloride, and extracted repeatedly with ethyl acetate. The combined extracts are washed with saturated aqueous sodium chloride solution, dried, and evaporated. The residue is chromatographed on 3 g. of acid-washed silica gel (Silicar CC4), eluting with 50 ml. of ethyl acetate and then with 50 ml. of 1% methanol in ethyl acetate, collecting 10 ml. fractions. The faster moving fractions are combined and evaporated to give racemic PGF$_{3\alpha}$ ; same mobility as optically active PGF$_{3\alpha}$ on TLC silica gel and silver-nitrate impregnated silica gel plates with the A IX system twice; mass spectrum spectral peaks same as for optically active PGF$_{3\alpha}$ . The slower moving fractions are combined and evaporated to give racemic PGF$_{3\beta}$ ; m.p. 85°–92° C.; same mobility as optically active PGF$_{3\beta}$ on TLC silica gel plates as for PGF$_{3\beta}$ ; mass spectrum spectral peaks same as for optically active PGF$_{3\beta}$ .

Substituting the racemic PGE$_3$ by the d- and l- forms. there are obtained the d- and l- forms of PGF$_{3\alpha}$ and PGF$_{3\beta}$ .

EXAMPLE 8

Racemic 15-epi-PGF$_{3\alpha}$ and racemic 15-epi-PGF$_{3\beta}$

Following the procedure of Example 7, 20 mg. of racemic 15-epi-PGE$_3$ is reduced with sodium borohydride to give racemic 15-epi-PGF$_{3\alpha}$ and racemic 15-epi-PGF$_{3\beta}$ , separated by chromatography on silicar CC4, eluting successively with 50, 75, and 100% ethyl acetate in Skellysolve B.

Substituting the racemic 15-epi-PGE$_3$ by the d- and l-forms, there are obtained the d- and l-forms of 15-epi-PGF$_{3\alpha}$ and 15-epi-PGF$_{3\beta}$ .

Following the procedure of Example 7, the racemic and optically active forms of 8-iso-PGE$_3$ and 8-iso-15-epi-PGE$_3$ are each reduced to the alpha and beta isomers of the corresponding racemic and optically active forms of 8-iso-PGE$_3$ and 8-iso-15-epi-PGF$_3$, respectively, the alpha and beta pairs being separated in each as described in Examples 7 or 8.

Also following the procedure of Example 7, each of the racemic and optically active forms of PGE$_3$-type compounds, 5,6,17,18-dehydro-PGE$_3$, 5,6,17,18-dehydro-15-epi-PGE$_3$, 5,6,17,18-dehydro-8-iso-PGE$_3$, 5,6,17,18-dehydro-8-iso-15-epi-PGE$_3$, and each of the other 5,6,17,18-dehydro-PGE$_3$-type compounds defined above is reduced to the corresponding racemic and optically active forms of the alpha and beta isomers of the corresponding PGF$_3$-type and 5,6,17,18-dehydro-PGF$_3$-type compound. In each case, the alpha and beta isomers are separated as described in Examples 7 or 8.

EXAMPLE 9

Racemic 5,6,17,18,-dehydro-PGA$_3$ (S) and racemic 5,6,17,18-dehydro-15-epi-PGA$_3$ (R)

Endo-6-(1,2-dimesyloxyhepty-4-ynyl)-2-(6-carboxyhex-2-yn-60-yl)bicyclo[3.1.0]hexan-3-one $\beta,\beta,\beta$-trichloroethyl ester is dissolved in 75 ml. of acetone to which is added 10 ml. of water and 20 ml. of saturated sodium bicarbonate solution. This mixture is refluxed under nitrogen for 4 hours. After acidification with one normal hydrochloric acid, the mixture is extracted with ethyl acetate, and the extracts are washed, dried, and evaporated to give the $\beta,\beta,\beta$-trichloroethyl ester of racemic 5,6,17,18-dehydro-PGA$_3$, and the $\beta,\beta,\beta$-trichloroethyl ester of racemic 5,6,17,18-dehydro-15-epi-PGA$_3$. These esters are transformed to racemic 5,6,17,18-dehydro-PGA$_3$ and racemic 5,6,17,18-dehydro-15-epi-PGA$_3$ by the procedure of Example 2, the racemic 5,6,17,18-dehydro-PGA$_3$ and racemic 5,6,17,18-dehydro-15-epi-PGA$_3$ being purified by the procedure of Pike et al., above cited.

The racemates are separated into the d- and l-forms by the procedures given above.

Following the procedure of Example 9 and using each of the above defined exo and endo, alpha and beta, acetylenic bicyclo[3.1.0]hexane glycol mesylate $\beta,\beta,\beta$-trichloroethyl esters, there are obtained each of the corresponding 5,6,17,18-dehydro-PGA$_3$-type compounds including 5,6,17,18-dehydro-PGA$_3$, 5,6,17,18-dehydro-15-epi-PGA$_3$, 5,6,17,18-dehydro-8-iso-PGA$_3$, and 5,6,17,18-dehydro-8-iso-15-epi-PGA$_3$ in the racemic and optically active forms.

Each of the above-defined PGA$_3$-type compounds and 5,6,17,18-dehydro-PGA$_3$-type compounds is also prepared from the corresponding PGE$_3$-type and 5,6,17,18-PGA$_3$-type compound by acetic acid dehydration as described by Pike et al., above cited, and in British Specification No. 1,097,533.

EXAMPLE 10

Racemic PGB$_3$

A solution of racemic PGE$_3$ (200 mg.) in 100 ml. of 50% aqueous ethanol containing 10 grams of potassium hydroxide is kept at 25° C. for 10 hours under notrogen. Then, the solution is cooled to 10° C. and neutralized by addition of 3 normal hydrochloric acid at 10°C. The resulting solution is extracted repeatedly with ethyl acetate, and the combined ethyl acetate extracts are washed with water and then with saturated aqueous sodium chloride solution, dried, and evaporated to give racemic PGB$_3$.

Following the procedure of Example 10, racemic PGA$_3$, d-PGA$_3$, and l-PGA$_3$ are trnasformed to racemic PGB$_3$, d-PGB$_3$, and l-PGB$_3$.

Also following the procedure of Example 10, each of the above defined PGE$_3$-type compounds and each of the above-defined PGA$_3$-type compounds is transformed to the corresponding PGB$_3$-type compound, including 15-epi-PGB$_3$, 5,6,17,18-dehydro-PGB$_3$, and 5,6,17,18-dehydro-15-epi-PGB$_3$, in the racemic and optically active forms.

EXAMPLE 11

Racemic 8-iso-PGE$_3$ from racemic PGE$_3$

A solution of 1.00 g. of racemic PGE$_3$ and 5 g. of potassium acetate in 100 ml. of 95% ethanol is allowed to stand at room temperature under nitrogen for 6 days; then is concentrated by evaporation under reduced pressure to about one third volume. The concentrated mixture is diluted with 75 ml. of cold water and dilute hydrochloric acid is added until the mixture reaches pH 3. The acidified mixture is extracted twice with ethyl acetate, then is saturated with sodium chloride and extracted once more with ethyl acetate. The ethyl acetate extracts are combined, washed with saturated aqueous sodium chloride, dried over sodium sulfate, and evaporated under reduced pressure, then dried under a stream of nitrogen to remove acetic acid from the residue. Thin layer chromatographic (TLC) analysis shows that the residue comprises a mixture of racemic PGE$_3$ and racemic 8-iso PGE$_3$. The residue is chromatographed on 200 g. of Silicar CC4, eluting with 500 ml. 40%, 500 ml. 50%, 250 ml. 60%, and 250 ml. 100% ethyl acetate in cyclohexane, collecting 50-ml. fractions. Fractions containing 8-iso PGE$_3$ as determined by TLC are evaporated to give racemic 8-iso-PGE$_3$.

By substituting the recemic PGE$_3$, by d- and l-PGE$_3$, there are obtained d- and l-8-iso-PGE$_3$.

EXAMPLE 12

Racemic PGE$_3$ from racemic 8-iso-PGE$_3$

The procedure of Example 11 is followed, using as a starting material racemic 8-iso-PGE$_3$ rather than racemic PGE$_3$. Substantially the same product mixture is obtained from which racemic PGE$_3$ is isolated by pooling and evaporating the fractions shown by TLC to contain racemic PGE$_3$, the slower moving component.

Following the procedure of Examples 11 or 12, each of the PGE$_3$-type, 8-iso-PGE$_3$-type, 5,6,17,18-dehydro-PGE$_3$-type, and 5,6,17,18-dehydro-8-iso-PGE$_3$-type compounds defined above is transformed to a mixture of alpha and beta isomers, the two isomers then being separated as described in Examples 11 and 12.

EXAMPLE 13

Racemic 15-methyl-PGF$_{3\alpha}$ Methyl ester [IXa (S)]

2,3-Dichloro-5,6-dicyano-1,4-benzoquinone (463 mg.) is added to a solution of racemic PGF$_{3\alpha}$ (600 mg.) in 30 ml. of dioxane. The mixture is stirred 24 hours at 50° C. under nitrogen, and then is cooled to 20° C. and filtered. The filtered solids are washed with dichloromethane. Evaporation of the combined filtrate and washings at reduced pressure gives a residue which is chromatographed on 150 g. of silica gel (Silicar CC4; Mallincrodt), eluting with 50% ethyl acetate in Skellysolve B (a mixture of isomeric hexanes). The eluates are evaporated and the residues containing racemic 15-oxo-PGF$_{3\alpha}$ (as shown by infrared analysis or by (TLC) are combined.

There is next prepared a trimethyl silyl derivative represented by Formula XXXVIII of Chart F. A mixture of hexamethyldisilazane (11 ml.) and trimethylchlorosilane (2.2 ml.) is added to a solution of the above racemic 15-oxo-PGF$_3$ (545 mg.) in 55 ml. of tetrahydrofuran. This mixture is stirred 16 hours at 25° C. under nitrogen, and is then filtered. The filtrate is evaporated under reduced pressure. Xylene (50 ml.) is added to the residue and the mixture is evaporated at 60° C. under reduced pressure. This addition of xylene and evaporation is repeated twice. The resulting residue is the tris-(trimethylsilyl) derivative of racemic 15-oxo-PGF$_{3\alpha}$.

Racemic 15-methyl-PGF$_{3\alpha}$ is obtained as follows.

A 3 molar diethyl ether solution of methylmagnesium bromide (0.55 ml.) is added dropwise to a stirred solution of the tris-(trimethylsilyl) derivative of racemic 15-oxo-PGF$_{3\alpha}$ (850 mg.) in 25 ml. of diethyl ether at 25° C. The mixture is stirred 30 minutes at 25° C., after which an additional 0.2 ml. of the methylmagnesium bromide solution is added and stirring is continued an additional 30 minutes. The resulting reaction mixture is poured into 75 ml. of saturated aqueous ammonium chloride solution at 0° C. After stirring several minutes, the mixture is extracted repeatedly with diethyl ether. The combined diethyl ether extracts are washed with saturated aqueous sodium chloride solution and then dried with anhydrous sodium sulfate. Evaporation of the diethyl ether gives a hellow oil which is dissolved in 45 ml. of ethanol. That solution is diluted with 30 ml. of water, and the mixture is stirred 4 hours at 25° C. The ethanol in the resulting solution is evaporated at reduced pressure, and the aqueous residue is saturated with sodium chloride and then extracted with ethyl acetate. The extract is washed with saturated aqueous sodium chloride solution, dried with anhydrous sodium sulfate, and evaporated under reduced pressure to give a mixture of racemic 15-methyl-PGE$_{3\alpha}$ and racemic 15-methyl-15(R)-PGF$_{3\alpha}$.

The mixture of racemic 15-methyl-PGF$_{3\alpha}$ and racemic 15-methyl-15(R)-PGF$_{3\alpha}$ is dissolved in 50 ml. of diethyl ether and cooled to 0° C. Excess diazomethane dissolved in diethyl ether is then added, and the mixture is maintained 5 minutes at 0° C. and then 5 minutes at 25° C. The solution is evaporated in a stream of nitrogen, and the residue is chromatographed on 550 g. of neutral silica, eluting with 75% ethyl acetate in Skellysolve B. Evaporation of eluate fractions gives, successively, racemic 15-methyl-15(R)-PGF$_{3\alpha}$ methyl ester, a mixture of racemic 15-methyl-15(R)-PGF$_{3\alpha}$ methyl ester and racemic 15-methyl-PGF$_{3\alpha}$ methyl ester, and racemic 15-methyl-PGF$_{3\alpha}$ methyl ester.

The above racemate can be resolved into the d- and l- forms by the procedures given above. The d- and l-forms are also obtained by substituting the racemic starting compound by the d- and l-forms thereof.

EXAMPLE 14

Racemic 15-methyl-PGE$_3$ methyl ester

A solution of racemic 15-methyl-PGF$_{3\alpha}$ methyl ester (80 mg.) in 40 ml. of acetone is cooled to −20° C. To it is added Jones reagent (0.1 ml. of a solution of 21 g. of chromic anhydride, 60 ml. of water, and 17 ml. of concentrated sulfuric acid), precooled to 0° C., with vigorous stirring. After 5 minutes at −10° C., thin layer chromatography on silica gel (acetic acid:methanol: chloroform; 5:5:90) of a small portion of the reaction mixture indicates about 50% reaction completion. An additional 0.06 ml. of Jones reagent is added to the still cold reaction mixture with stirring, and the mixture is stirred an additional 5 minutes at −10° C. Isopropyl alcohol (1 ml.) is added to the cold reaction mixture. After 5 minutes, the mixture is filtered through a layer of diatomaceous silica (Celite). The filtrate is concentrated at reduced pressure, and the residue is mixed with 5 ml. of saturated aqueous sodium chloride solution. The mixture is extracted repeatedly with ethyl acetate, and the combined extracts are washed with saturated aqueous sodium chloride solution, dried with anhydrous sodium sulfate, and concentrated at reduced pressure. The residue is chromatographed on 20 g. of neutral silica gel, eluting with 50% ethyl acetate in Skellysolve B. Evaporation of the eluates gives the product, racemic 15-methyl-PGE$_3$ methyl ester.

The above racemate can be resolved into the d- and l-forms by the procedures given above. The d- and l-forms are also obtained by substituting the racemic starting compound by the d- and l-forms thereof.

Following the procedure of Example 14, there is substituted for the 15-methyl-PGF$_{3\alpha}$ methyl ester, the free acid, the ethyl ester, the propyl ester, the octyl ester, the cyclopentyl ester, the benzyl ester, the phenyl ester, the 2,4-dichlorophenyl ester, the 2-tolyl ester, or the $\alpha,\alpha,\alpha$-trichloroethyl ester, there are obtained the corresponding racemic, d- and l-15-methyl-PGE$_3$ compounds.

Following the procedure of Example 14, but substituting for the 15-methyl-PGF$_{3\alpha}$ methyl ester, the methyl ester of each of the 15-methyl -PGF$_{3\beta}$, 5,6,17,18-dehydro-PGF$_{3\alpha}$, 5,6,17,18-dehydro-PGF$_{3\beta}$ compounds in their various R or S configurations and optical isomers are transformed to the corresponding PGE$_3$ compound.

Following the procedure of Example 14, each of the various 15-alkyl-PGF$_{3\alpha}$ methyl ester compounds, including the 15-ethyl, 15-propyl, 15-butyl, and 15-substituted isomeric forms of propyl and butyl, is transformed to the corresponding PGE$_3$ compound.

Also following the procedure of Example 14, each of the 15-alkyl PGE$_3$-type acids and esters within the scope of Formula IXa (Chart E) is transformed to a 15-alkyl PGE$_3$-type acid or ester encompassed by Formula VIIIa.

EXAMPLE 15

Racemic 15-methyl-PGA$_3$ methyl ester (XA) A mixture of racemic 15-Methyl-PGE$_3$ methyl ester (5 mg.), dicyclohexycarbodiimide (20 mg.), copper (II) chloride dihydrate (2 mg.), and diethyl ether (2 ml.) is stirred under nitrogen at 25° C. for 16 hours. Then, additional dicyclohexylcarbodiimide (20 mg.) is added, and the mixture is stirred an additional 32 hours at 25° C. under nitrogen. The resulting mixture is filtered, and the filtrate is evaporated under reduced pressure. The residue is chromatographed by preparative thin layer chromatography with the A-IX system to give racemic 15-methyl-PGA$_3$ methyl ester.

Following the procedure of Example 15, but substituting for the PGE$_3$ compound, the methyl esters of 15-methyl-5,6,17,18-dehydro-PGE$_3$, there is obtained the corresponding methyl esters of 15methyl-5,6,17,18-dehydro-PGA$_3$.

Each of the above racemates can be resolved into the d- and l-forms by the procedures given above. The d- and l-forms are also obtained by substituting the racemic starting compound by the d- and l-forms thereof.

By substituting the 15-methyl PGE$_3$ compound by the corresponding 15-ethyl, 15-propyl, 15-butyl, and 15-substituted isomeric forms of propyl and butyl, there are obtained the corresponding PGA$_3$ compounds.

Each of the above racemates can be resolved into the d- and l-forms by the procedures given above. The d- and l-forms are also obtained by substituting the racemic starting compound by the d- and l-forms thereof.

EXAMPLE 16

15-Methyl PGB$_3$ methyl ester

Following the procedure of Example 10, substituting the racemic PGE$_3$ methyl ester by racemic 15-methyl PGE$_3$ methyl ester, there is obtained 15-methyl PGB$_3$ methyl ester.

By substituting the methyl ester by the free acid, the ethyl ester, the propyl ester, the octyl ester, the cyclopentyl ester, the phenyl ester, the 2,4-dichlorophenyl ester, the 2-tolyl ester, or the $\beta$, $\beta$, $\beta$-trichloroethyl ester, there are obtained the corresponding 15-methyl-PGB$_3$ compounds.

By substituting the above free acid and esters by the corresponding free acid and esters of 5,6,17,18-dehydro-PGE$_3$ in their various R and S configurations and isomeric forms, there are obtained the corresponding free acid and esters of the corresponding PGB$_3$ compounds.

By substituting the 15-methyl-PGE$_3$ compounds by the corresponding 15-ethyl, 15-propyl, 15-butyl, and 15-substituted isomeric forms of propyl and butyl, there are obtained the corresponding 15-substituted PGB$_3$ compounds.

I claim:

1. A racemic mixture of a compound of the formula:

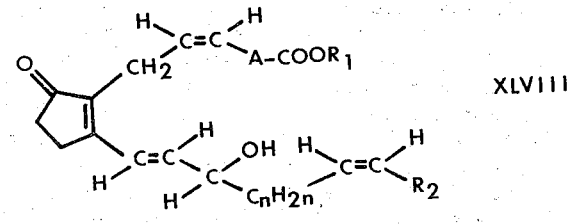

XLVIII and its mirror image, wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or $\beta,\beta$, $\beta$-trichloroethyl; wherein $R_2$ is alkyl of one to 4 carbon atoms, inclusive, substituted with zero to 3 fluoro; wherein $n$ is an integer of one to 4, inclusive; wherein A is alkylene of one to 10 carbon atoms, inclusive, substituted with zero to 2 fluoro, and with one to 5 carbon atoms, inclusive, between —COOR$_1$ and $$=C{\overset{H}{\underset{\ }{\diagdown}}} ;$$

or a pharmacologically acceptable salt thereof when $R_1$ is hydrogen.

2. A racemic mixture according to claim 1 wherein $R_1$ is hydrogen or alkyl of one to 4 carbon atoms, or a pharmacologically acceptable salt thereof when $R_1$ is hydrogen.

3. A racemic mixture according to claim 2 wherein the side-chain hydroxy is in S configuration.

4. A racemic mixture according to claim 3 wherein $n$ is one.

5. A racemic mixture according to claim 4 wherein A is trimethylene.

6. A racemic mixture according to claim 5 wherein $R_2$ is ethyl.

7. Racemic $PGB_3$, a racemic mixture according to claim 6 wherein $R_1$ is hydrogen.

8. An optically active compound of the formula:

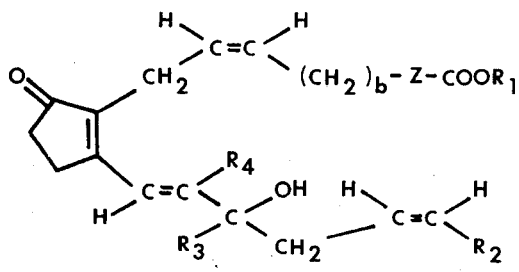

or a racemic compound of that formula and the mirror image thereof, wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or $\beta,\beta,\beta$-trichloroethyl; wherein $R_2$ is alkyl of one to 4 carbon atoms, inclusive, substituted with zero to 3 fluoro; wherein $R_3$ and $R_4$ are hydrogen or alkyl of one to 4 carbon atoms, inclusive; wherein Z is ethylene substituted by one or 2 fluoro; wherein $b$ is zero, one, 2, or 3; or a pharmacologically acceptable salt thereof when $R_1$ is hydrogen.

9. An optically active compound according to claim 8 wherein the side-chain hydroxy is in S configuration, and wherein $R_1$ is hydrogen or alkyl of one to 4 carbon atoms, or a pharmacologically acceptable salt thereof when $R_1$ is hydrogen.

10. An optically active compound according to claim 9 wherein $R_2$ is ethyl and $b$ is one.

11. An optically active compound according to claim 10 wherein Z is ethylene substituted with 2 fluoro on the carbon atom alpha to the carboxylate function.

12. An optically active compound according to claim 11 wherein $R_3$ and $R_4$ are hydrogen.

13. An optically active compound according to claim 11 wherein $R_3$ is alkyl of one to 4 carbon atoms, inclusive, and $R_4$ is hydrogen.

* * * * *

UNITED STATES PATENT AND TRADEMARK OFFICE
CERTIFICATE OF CORRECTION

PATENT NO. : 3,954,851
DATED : May 4, 1976
INVENTOR(S) : Udo F. Axen

It is certified that error appears in the above-identified patent and that said Letters Patent are hereby corrected as shown below:

Column 2, line 56: "i-[(2β-octyl)cyclopent-1α-yl]heptanoic" should read: -- 7-[(2β-octyl)cyclopent-1α-yl]heptanoic--.

Column 4, line 45: "formulas VIII, IXX, and X" should read: --formulas VIII, IX, and X--.

Column 9, line 11: "the $PGF_3$ -type" should read: --the $PGF_{3\alpha}$-type--.

Column 9, lines 48-49: "A is $-(CH)_b-Z-$" should read: --A is $-(CH_2)_b-Z-$ --.

Column 9, lines 57-58: "$-CHF-CHh_2-$," should read: -- $-CHF-CH_2-$ --.

Column 13, Chart A-1, formula VIIId should appear as follows:

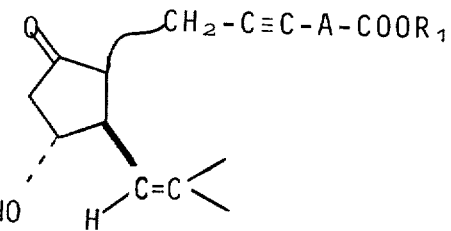

Column 15-16, Chart A-1, formula XI d should appear as follows:

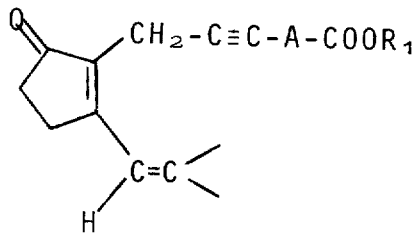

Column 22, lines 30-31: "or $HOCC-CH_2-Z-COOCH_3$," should read: --or $HOCC-CH_2CH_2-Z-COOCH_3$,--.

UNITED STATES PATENT AND TRADEMARK OFFICE
CERTIFICATE OF CORRECTION

PATENT NO. : 3,954,851
DATED : May 4, 1976
INVENTOR(S) : Udo F. Axen

It is certified that error appears in the above–identified patent and that said Letters Patent are hereby corrected as shown below:

Column 22, line 48: "primary alcohols XXII" should read:
    --primary alcohol XXII--.
Column 23, line 15: "vicinal hydroxy group of" should read:
    --vicinal hydroxy groups of--.
Column 23, line 54: "and this is recycled" should read: --and
    thus is recycled--.
Column 23, lines 56-57: "the bis-methyl esters," should read:
    --the bis-mesyl esters,--.
Column 24, line 25: "alpha XXV given alpha Xd" should read:
    --alpha XXV gives alpha Xd--.
Column 25, line 12: "even through the number" should read:
    --even though the number--.
Column 25, lines 35-45, formula IX a: formula should appear
    as follows:

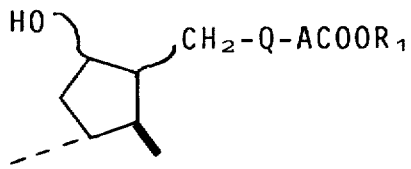

Column 26, line 67: "Formula IXa is Chart E" should read:
    --Formula IXa in Chart E--.
Column 27, lines 54-55: "or methylphenylsilyl." should read:
    --or methylphenylbenzylsilyl.--.
Column 28, line 11: "swine ling [see Arkiv for Kemi 25, 293
    (1966)]These" should read: --swine lung [see Arkiv för
    Kemi 25, 293 (1966)]. These --.
Column 34, line 23: formula VIIIe, IXe, VIIId," should read:--
    formula VIIIe, IXe, Xe, XIe, VIIId,--.
Column 35, line 59: "and endo-6-hydroxymethylvicyclo[3.1.0]-"
    should read: --and endo-6-hydroxymethylbicyclo[3.1.0]- --.
Column 37, line 35: "3-one (XLIII)" should be deleted.

UNITED STATES PATENT AND TRADEMARK OFFICE
CERTIFICATE OF CORRECTION

PATENT NO. : 3,954,851
DATED : May 4, 1976
INVENTOR(S) : Udo F. Axen

It is certified that error appears in the above-identified patent and that said Letters Patent are hereby corrected as shown below:

Column 37, line 43: "to -5° to 31 10° C." should read: --to -5° to -10° C.--.
Column 37, line 60: "5.3 g. of ketone XLII" should read: --5.3 g. of ketone XLIII--.
Column 37, line 63: "3H at 0.9-1.36 δ (triplet)." should read: --3H at 0.9-1.3 δ (triplet).--.
Column 39, lines 62-63: "ethyl acetate-Skellysolve B 90:10, B 90:10, ethyl acetate," should read: --ethyl acetate-Skellysolve B 90:10, ethyl acetate,--.
Column 44, lines 15-16: "Endo-6-(1,2-dimesyloxy-hepty-4-ynyl)-2-(6-carboxyhex-2-yn-60-yl)bicyclo[3.1.0]hexan-3-one" should read: --Endo-6-(1,2-dimesyloxyhepty-4-ynyl)-2-(6-carboxyhex-2-yn-α-yl)bicyclo[3.1.0]hexan-3-one --.
Column 46, line 1: "15 oxo-PGF$_3$" should read: -- 15-oxo-PGF$_{3\alpha}$ --
Column 46, line 58: "cooled to -20° C." should read: --cooled to -10° C. --.
Column 47, line 46: "(XA)" should read: --(Xa)--.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks